United States Patent [19]

Bender et al.

[11] Patent Number: 5,753,653
[45] Date of Patent: May 19, 1998

[54] METALLOPROTEINASE INHIBITORS, PHARMACEUTICAL COMPOSITIONS CONTAINING THEM AND THEIR PHARMACEUTICAL USES

[75] Inventors: Steven L. Bender, Oceanside; Michael J. Melnick, San Diego, both of Calif.

[73] Assignee: Agouron Pharmaceuticals, Inc., LaJolla, Calif.

[21] Appl. No.: 759,713

[22] Filed: Dec. 6, 1996

Related U.S. Application Data

[60] Provisional application No. 60/041,496 Dec. 8, 1995.

[51] Int. Cl.[6] .................. C07D 403/14; C07D 403/02; A61K 31/54; A61K 31/535
[52] U.S. Cl. .................. 514/227.5; 514/227.8; 514/235.5; 514/237.5; 514/255; 514/256; 514/269; 544/58.2; 544/58.4; 544/111; 544/158; 544/161; 544/131; 544/319; 544/331; 544/360; 544/383
[58] Field of Search .................. 544/8, 58.2, 58.4, 544/111, 158, 161, 131, 319, 335, 360, 383; 514/227.5, 227.8, 235.5, 237.5, 235, 256, 269

[56] References Cited

U.S. PATENT DOCUMENTS

| | | | |
|---|---|---|---|
| 4,032,639 | 6/1977 | Freed et al. | 424/251 |
| 5,183,900 | 2/1993 | Galardy et al. | 548/495 |
| 5,189,178 | 2/1993 | Galardy et al. | 514/357 |
| 5,455,258 | 10/1995 | MacPherson et al. | 514/357 |
| 5,506,242 | 4/1996 | MacPherson et al. | 514/336 |
| 5,552,419 | 9/1996 | MacPherson et al. | 514/357 |

FOREIGN PATENT DOCUMENTS

| | | |
|---|---|---|
| 276436 | 8/1988 | European Pat. Off. |
| 438223 | 7/1991 | European Pat. Off. |
| 606046 | 7/1994 | European Pat. Off. |
| 757037 | 2/1997 | European Pat. Off. |
| 757984 | 2/1997 | European Pat. Off. |
| WO 92/06966 | 4/1992 | WIPO |
| WO 92/09563 | 6/1992 | WIPO |
| WO 92/21360 | 12/1992 | WIPO |
| WO 94/02466 | 2/1994 | WIPO |
| WO 94/24140 | 10/1994 | WIPO |
| WO 96/00214 | 1/1996 | WIPO |
| WO 96/27583 | 9/1996 | WIPO |
| WO 96/33172 | 10/1996 | WIPO |

OTHER PUBLICATIONS

E. von Felder et al., *Helv. Chim. Acta*, vol. 43, No. 117 (1960), pp. 888–894.

Aebischer et al., "Synthesis and NMDA Antagonistic Properties of the Enantiomers of 4-(3-Phosphonopropyl)piperazine-2-carboxylic Acid (CPP) and of the Unsaturated Analogue (E)-4-(3-Phosphonoprop-2-enyl)piperazine-2-carboxylic Acid (CPP-ene)," *Helvetica Chimica Acta*, vol. 72 (1989), pp. 1043–1051.

Brunwin et al., "Total Synthesis of Nuclear Analogues of 7-Methylcephalosporin," *J.C.S. Perkin I* (1973), pp. 1321–1328.

Knight et al., "A novel coumarin-labelled peptide for sensitive continuous assays of the matrix metalloproteinases," *FEBS*, vol. 296, No. 3 (1992), pp. 263–266.

Menegatti et al., "Inhibition of Serine Proteinases by Tetra-p-Amidinophenoxy-neo-Pentane: Thermodynamic and Molecular Modeling Study," *J. Enzyme Inhibition*, vol. 2 (1987), pp. 23–30.

Johnson, "Collagenase Inhibitors," *Drug News & Perspectives*, vol. 3, No. 8 (1990), pp. 453–458.

Henderson et al., "Design of Inhibitors of Articular Cartilage Destruction," *Drugs of the Future*, vol. 15, No. 5 (1990), pp. 495–508.

Harrison et al., "A Semicontinuous, High-Performance Liquid Chromatography-Based Assay for Stromelysin," *Analytical Biochemistry*, vol. 180 (1989), pp. 110–113.

Shinmei et al. "The Mechanism of Cartilage Degradation in Osteoarthritic Joints," *Seminars in Arthritis and Rheumatism*, vol. 19, No. 4, Suppl. 1 (1990), pp. 16–20.

Weingarten et al., "Spectophotometric Assay for Vertebrate Collegenase," *Analytical Biochemistry*, vol. 147 (1985) pp. 437–440.

Davies et al., "A Synthetic Matrix Metalloproteinase Inhibitor Decreases Tumor Burden and Prolongs Survival of Mice Bearing Human Ovarian Carcinoma Xenografts," *Cancer Research*, vol. 53 (1993), pp. 2087–2091.

Brinckerhoff, "Joint Destruction in Arthritis: Metalloproteinases in the Spotlight," *Arthritis & Rheumatism*, vol. 34, No. 9 (1991), pp. 1073–1075.

(List continued on next page.)

*Primary Examiner*—Matthew V. Grumbling
*Attorney, Agent, or Firm*—Finnegan, Henderson, Farabow, Garrett & Dunner, L.L.P.

[57] ABSTRACT

The invention relates to compounds of the formula I

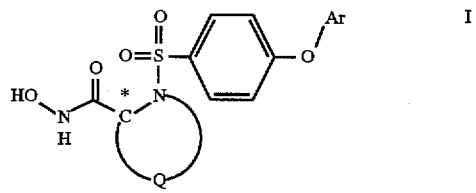

in which Q is a divalent radical having four ring atoms which together with C* and N form a six-membered ring, each of these four ring atoms being unsubstituted or substituted by a suitable substituent and at least one being a heteroatom selected from O, N and S, with the remainder being carbon atoms; and Ar is an aryl or heteroaryl group. The invention further relates to pharmaceutically acceptable prodrugs and pharmaceutically acceptable salts of these compounds. The invention also relates to methods of inhibiting the activity of metalloproteinases, especially MMPs or TNF-α, by administering a compound of the formula I or a salt or prodrug thereof. The invention further relates to pharmaceutical compositions comprising an effective amount of these compounds, salts, and prodrugs.

22 Claims, No Drawings

OTHER PUBLICATIONS

Morrison, "Kinetics of the Reversible Exhibition of Enzyme–Catalysed Reactions by Tight–Binding Inhibitors," *Biochem. Biophys. Acta*, vol. 185 (1969), pp. 269–286.

Lohmander et al., "Metalloproteinases, Tissue Inhibitor, Proteoglycan Fragments in Knee Synovial Fluid in Human Osteoarthritis," *Arthritis & Rheumatism*, vol. 36, No. 2 (1993), pp. 181–187

Schwartz et al., "Synthetic Inhibitors of Bacterial and Mammalian Interstitial Collagenases," *Progress in Medicinal Chemistry*, vol. 29 (1992), pp. 271–334.

METALLOPROTEINASE INHIBITORS, PHARMACEUTICAL COMPOSITIONS CONTAINING THEM AND THEIR PHARMACEUTICAL USES

This application claims the benefit of Provisional application Ser. No. 60/041,496, filed Dec. 8, 1995, which was converted from application Ser. No. 08/569,766.

INTRODUCTION

The present invention relates to compounds which inhibit metalloproteinases, particularly matrix metalloproteinases and tumor necrosis factor-α convertase, and their pharmaceutically acceptable salts and pharmaceutically acceptable prodrugs. The invention further relates to the uses of these compounds, salts and prodrugs for the therapeutic treatment of humans or animals.

Matrix metalloproteinases ("MMPs") are a family of enzymes, including, but not limited to, collagenases, gelatinases, matrilysin, and stromelysins, which are involved in the degradation and remodelling of connective tissues. These enzymes are found in a number of cell types that are found in or associated with connective tissue, such as fibroblasts, monocytes, macrophages, endothelial cells and metastatic tumor cells. They also share a number of properties, including zinc and calcium dependence, secretion as zymogens, and 40–50% amino acid sequence homology.

Matrix metalloproteinases degrade the protein components of the extracellular matrix, i.e. the protein components found in the linings of joints, interstitial connective tissue, basement membranes, cartilage and the like. These proteins include collagen, proteoglycan, fibronectin and lamanin.

Collagen is the major structural protein of mammalian tissue, comprising one-third of the total protein in mammalian organisms, and is an essential component of many matrix tissues, including cartilage, bone, tendons and skin. Interstitial collagenases catalyze the initial (rate-limiting) cleavage of native collagen types I, II, III and X. These enzymes cleave collagen into two fragments which spontaneously denature at physiological temperature. Denaturation of collagen involves conversion of the rigidly coiled helix to a random coil referred to as gelatin. These gelatin (denatured collagen) fragments are then subject to further cleavage and degradation by less specific enzymes. The net result of collagenase cleavage is thus the loss of structural integrity in the matrix tissue (collagen collapse), an essentially irreversible process.

The gelatinases include two distinct yet highly related enzymes: a 72-kiloDalton (kDa) enzyme and a 92-kiloDalton enzyme. The former is released by fibroblasts while the latter is released by mononuclear phagocytes, neutrophils, corneal epithelial cells, tumor cells, cytotrophoblasts and keratinocytes. Both enzymes degrade gelatins (denatured collagens), collagen types IV (basement membrane) and V, fibronectins (high molecular weight multifunctional glycoproteins found in soft connective tissue and basement membranes) and insoluble elastin (highly cross-linked hydrophobic proteins found in load bearing fibers of mammalian connective tissue).

Stromelysins (1 and 2) cleave a broad range of matrix substrates, including lamanin, fibronectins, proteoglycans and collagen types IV and IX (non-helical).

Matrilysin (putative metalloproteinase or PUMP) also degrades a wide variety of matrix substrates, including proteoglycans, gelatins, fibronectins, elastins and lamanin. Matrilysin has been found in mononuclear phagocytes, rat uterine explants and tumor cells.

In normal tissues, the activity of matrix metalloproteinases is tightly regulated. As a result, the breakdown of connective tissue mediated by these enzymes is generally in a dynamic equilibrium with synthesis of new matrix tissue.

In a number of pathological disease conditions, however, deregulation of matrix metalloproteinase activity leads to the uncontrolled breakdown of extracellular matrix. These disease conditions include arthritis (e.g., rheumatoid arthritis and osteoarthritis), periodontal disease, aberrant angiogenesis, tumor metastasis and invasion, tissue ulceration (e.g., corneal ulceration, gastric ulceration or epidermal ulceration), bone disease, HIV-infection and complications from diabetes.

Administration of matrix metalloproteinase inhibitors has been found to reduce the rate of connective tissue degradation, thereby leading to a favorable therapeutic effect. For example, in *Cancer Res.*, vol. 53, p. 2087 (1993), a synthetic matrix metalloproteinase inhibitor was shown to have in vivo efficacy in a murine model for ovarian cancer with an apparent mode of action consistent with inhibition of matrix remodelling. The design and use of matrix metalloproteinase inhibitors is described in *Progress in Medicinal Chemistry*, vol. 29, pp. 271–334 (1992); *J. Enzyme Inhibition*, vol. 2, pp. 1–22 (1987); *Drug News & Prospectives*, vol. 3, pp. 453–458 (1990); *Arthritis and Rheumatism*, vol. 36, pp. 181–189 (1993); *Arthritis and Rheumatism*, vol. 34, pp. 1073–1075; *Seminars in Arthritis and Rheumatism*, vol. 19, Supplement 1, pp. 16–20 (February 1990); *Drugs of the Future*, vol. 15, pp. 495–508 (1990); and *J. Enzyme Inhibition*, vol. 2, pp. 1–22 (1987).

Matrix metalloproteinase inhibitors are also the subject of numerous patents and patent applications, including: U.S. Pat. No. 5,189,178; U.S. Pat. No. 5,183,900; European Patent Application No. 0 606 046; European Patent Application No. 0 438 223; European Patent Application No. 0 276 436; WIPO International Publication No. WO 92/21360; WIPO International Publication No. WO 92/06966; and WIPO International Publication No. WO 92/09563, the disclosures of each of which are incorporated herein by reference.

Tumor necrosis factor-α ("TNF-α") is a cytokine which is produced as a 28-kDa precursor and released in an active 17-kDa form. This active form can mediate a large number of deleterious effects in vivo, including inflammation, fever, cardiovascular effects, haemorrhage, coagulation and acute phase responses, similar to those seen during acute infections and shock states. Chronic administration of TNF-α can cause cachexia and anorexia; accumulation of excess of TNF-α can be fatal.

TNF-α convertase is a metalloproteinase involved in the biosynthesis of TNF-α. Inhibition of TNF-α convertase inhibits production of TNF-α.

Since excessive TNF-α production has been noted in several disease conditions characterized by MMP-mediated tissue degradation, including multiple sclerosis, arthritis and cancer, compounds which inhibit both MMPs and TNF-α convertase are especially advantageous for the treatment or prophylaxis of disease conditions in which both mechanisms are involved. Although compounds that both inhibit MMPs activity and TNF-α production have been disclosed in WIPO International Publication Nos. WO 94/24140 and WO 94/02466, the disclosures of which are herein incorporated by reference, there is still a need for effective MMP and/or TNF-α convertase inhibiting agents.

3

SUMMARY OF INVENTION

Because of their beneficial therapeutic effects, there is a need for effective inhibitors of metalloproteinase activity. The present invention is therefore directed to certain compounds that inhibit metalloproteinases, such as MMPs and TNF-α convertase, their pharmaceutically acceptable prodrugs and their pharmaceutically acceptable salts, pharmaceutical compositions containing the same and methods of using the same. Additional features and advantages of the invention will be set forth in the description which follows, and in part will be apparent from the description or may be learned from practice of the invention.

To achieve these and other advantages, the present invention provides compounds of the formula I

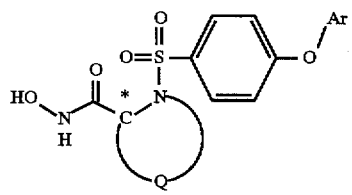

in which Q is a divalent radical having four ring atoms which together with C* and N form a six-membered ring, each of these four ring atoms being unsubstituted or substituted by a suitable substituent as defined below with at least one being a heteroatom selected from O, N and S, the remainder being carbon atoms; and Ar is an aryl or heteroaryl group; and pharmaceutically acceptable prodrugs thereof and pharmaceutically acceptable salts thereof.

Preferred compounds of the formula I include those having the formula I-a

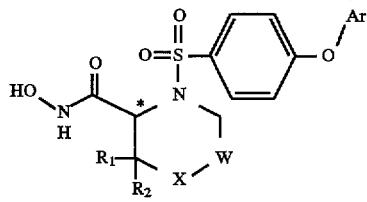

in which W and
X are each, independently of one another, $CH_2$, C=O, O, S, S=O, N—$R_3$ or $N^+(O^-)$-$R_4$, provided that W and X are not both $CH_2$; $R_1$ and $R_2$ are each, independently of one another, a hydrogen atom, a lower alkyl group, a hydroxycarbonyl group, an alkoxycarbonyl group, an alkylamino group or a dialkylamino group, or together $R_1$ and $R_2$ form a cycloalkyl ring or heterocycloalkyl ring; $R_3$ is a hydrogen atom or a suitable substituent as described below; $R_4$ is a lower alkyl group; and Ar is an aryl or heteroaryl group; and pharmaceutically acceptable prodrugs thereof and pharmaceutically acceptable salts thereof.

There is also provided a method of inhibiting the activity of a metalloproteinase, such as an MMP or TNF-α convertase, by administering a compound of the formula I or I-a or a pharmaceutically acceptable prodrug thereof or a pharmaceutically acceptable salt thereof. There is further provided a pharmaceutical composition comprising an effective amount of a compound of the formula I or I-a or a pharmaceutically acceptable salt thereof or pharmaceutically acceptable prodrug thereof. Particularly advantageous methods of making the compounds of the formula I-a and their salts and prodrugs are also described.

It is to be understood that both the foregoing general description and the following detailed description are exemplary and explanatory and are intended to provide illustration of the invention as claimed.

DETAILED DESCRIPTION AND PREFERRED EMBODIMENTS OF THE INVENTION

The present invention relates to compounds of the formula I

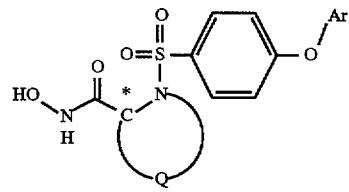

wherein
Q is a divalent radical having four ring atoms which together with C* and N form a six-membered ring, where each of these four ring atoms is unsubstituted or substituted by a suitable substituent and at least one of which is a heteroatom selected from O, N and S, and the remainder are carbon atoms; and Ar is an aryl or heteroaryl group;
or a pharmaceutically acceptable prodrug thereof or a pharmaceutically acceptable salt thereof.

The present invention preferably relates to compounds of the formula I-a

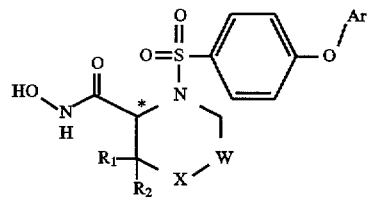

wherein:
W and X are each, independently of one another, $CH_2$, C=O, S, S=O, O, N—$R_3$ or $N^+(O^-)$-$R_4$, where
$R_3$ is a hydrogen atom or a suitable substituent, and
$R_4$ is a lower alkyl group, provided that W and X are not both $CH_2$;

$R_1$ and $R_2$ are each, independently of one another, a hydrogen atom, a lower alkyl group, a hydroxycarbonyl group, an alkoxycarbonyl group, an alkylaminocarbonyl group or a dialkylaminocarbonyl group, or $R_1$ and $R_2$ together form a cycloalkyl or heterocycloalkyl ring; and Ar is an aryl or heteroaryl group;
and pharmaceutically acceptable prodrugs thereof and pharmaceutically acceptable salts thereof.

As used in the present application, the following definitions apply:

"An alkyl group" is intended to mean a straight or branched chain monovalent radical of carbon and hydrogen atoms and having no unsaturation, such as methyl, ethyl, propyl, isopropyl, butyl, isobutyl, t-butyl, and the like, which may be unsubstituted (i.e., consisting only of carbon and hydrogen atoms) or substituted by one or more suitable substituents.

"An alkylene group" is intended to mean a straight- or branched-chain divalent radical of carbon and hydrogen atoms and having no unsaturation, such as methylene, ethylene, propylene and the like, which may be unsubstituted (i.e., consisting only of carbon and hydrogen atoms) or substituted by one or more suitable substituents.

"A suitable substituent" is intended to mean one or two chemically and pharmaceutically acceptable functional groups, i.e., one or two moieties that do not negate the inhibitory activity of the inventive compounds. Such suitable substituents may be routinely selected by those skilled in the art. Illustrative examples of suitable substituents include, but are not limited to, alkyl groups, hydroxy groups, oxo groups, mercapto groups, alkylthio groups, alkoxy groups, aryl or heteroaryl groups, aralkyl or heteroaralkyl groups, aralkoxy or heteroaralkoxy groups, carboxy groups, amino groups, alkyl- and dialkylamino groups, carbamoyl groups, alkylcarbonyl groups, alkoxycarbonyl groups, alkylaminocarbonyl groups, dialkylaminocarbonyl groups, arylcarbonyl groups, aryloxycarbonyl groups, alkylsulfonyl groups, an arylsulfonyl groups and the like.

"A lower alkyl group" is intended to mean an alkyl group as defined above which has from 1 to 7 chain carbon atoms, such as methyl, ethyl or propyl.

"A hydroxy group" is intended to mean the radical —OH.

"An amino group" is intended to mean the radical —NH$_2$.

"An alkylamino group" is intended to mean the radical —NHR where R is an alkyl group as defined above.

"A dialkylamino group" is intended to mean the radical —NR$_a$R$_b$ where R$_a$ and R$_b$ are each independently an alkyl group as defined above.

"An alkylcarbonyl group" is intended to mean the radical —C(O)R where R is an alkyl group as defined above.

"An alkoxy group" is intended to mean the radical —OR where R is an alkyl group as defined above. Illustrative examples include methoxy, ethoxy, propoxy and the like.

"An alkoxycarbonyl group" is intended to mean the radical —C(O)OR where R is an alkyl group as defined above.

"An alkylsulfonyl group" is intended to mean the radical —SO$_2$R where R is an alkyl group as defined above.

"An alkylaminocarbonyl group" is intended to mean the radical —C(O)NHR where R is an alkyl group as defined above.

"A dialkylaminocarbonyl group" is intended to mean the radical —C(O)NR$_a$R$_b$ where R$_a$ and R$_b$ are each independently an alkyl group as defined above.

"An aryl group" is intended to mean a monocyclic aromatic radical containing carbon atoms, preferably 6 ring carbon atoms, which may be unsubstituted (i.e., consisting only of carbon and hydrogen) or substituted by one or more suitable substituents as defined above.

"A heteroaryl group" is intended to mean a monocyclic aromatic radical containing carbon atoms, preferably 4 or 5 ring carbon atoms, and at least one heteroatom selected from nitrogen, oxygen and sulfur, which may be unsubstituted or substituted by one or more suitable substituents as defined above. Illustrative examples of unsubstituted heteroaryl groups include, but are not limited to, pyridyl, pyrazolyl, imidazolyl, furanyl and thiophenyl.

"A mercapto group" is intended to mean the radical —SH.

"An alkylthio group" is intended to mean the radical —SR where R is an alkyl group as defined above.

"A carboxy group" is intended to mean the radical —C(O)OH.

"A carbamoyl group" is intended to mean the radical —C(O)NH$_2$.

"A cycloalkyl group" is intended to mean a monocyclic radical containing carbon atoms, preferably 6 ring carbon atoms, and having no unsaturation, which may be unsubstituted (i.e., consisting only of carbon and hydrogen) or substituted by one or more suitable substituents as defined above.

"A heterocycloalkyl group" is intended to mean a monocyclic radical containing carbon atoms, preferably 4 or 5 ring carbon atoms, and at least one heteroatom selected from nitrogen, oxygen and sulfur, and having no unsaturation, which may be unsubstituted or substituted by one or more suitable substituents as defined above.

"An aralkyl group" is intended to mean the radical —R$_a$R$_b$ where R$_a$ is an alkylene group as defined above and R$_b$ is an aryl group as defined above.

"A heteroaralkyl group" is intended to mean the radical —R$_a$R$_b$ where R$_a$ is an alkylene group as defined above and R$_b$ is a heteroaryl group as defined above.

"An aralkoxy group" is intended to mean the radical —OR$_a$R$_b$ where R$_a$ is an alkyleneoxy group and R$_b$ is an aryl group as defined above.

"A heteroaralkoxy group" is intended to mean the radical —OR$_a$R$_b$ where R$_a$ is an alkyleneoxy group and R$_b$ is a heteroaryl group as defined above.

"A pharmaceutically acceptable salt" is intended to mean those salts that retain the biological effectiveness and properties of the free acids and bases and that are not biologically or otherwise unacceptable for pharmaceutical use.

"Therapeutically effective amount" is intended to mean that amount of a compound of the formula I or I-a, or a salt thereof or a prodrug thereof, which, when administered to a mammal in need thereof, is sufficient to effect treatment for a disease mediated by the activity of one or more metalloproteinases, for example MMPs such as stromelysin, matrilysin, gelatinase or collagenase, or TNF-α convertase. In other words, a "therapeutically effective amount" of a compound of the formula I or I-a, or salt or prodrug thereof, is an amount sufficient to inhibit the activity of one or more metalloproteinases such that a disease condition which is mediated by that activity is reduced or alleviated. The amount of a given compound of the formula I or I-a that will correspond to a "therapeutically effective amount" will vary depending upon factors such as the particular compound, the disease condition and the severity thereof, the identity of the mammal in need thereof, but can nevertheless be readily determined by one skilled in the art. "Treating" or "treatment" is intended to mean at least the mitigation of a disease condition in a mammal, such as a human, that is affected, at least in part, by the activity of one or more metalloproteinases, including MMPs, such as stromelysin, matrilysin, gelatinase or collagenase, and TNF-α convertase and includes:

(a) preventing the disease condition from occurring in a mammal, particularly when the mammal is found to be predisposed to leaving the disease condition but has not yet been diagnosed as having it;

(b) inhibiting the disease condition; and/or (c) alleviating the disease condition.

"Pharmaceutically acceptable prodrug" is intended to mean a compound that may converted under physiological conditions or by solovolysis to a compound of the formula I or I-a, or to a pharmaceutically acceptable salt thereof.

Preferably, in the above formula I-a, Ar is an aryl group. More preferably, Ar is an aryl group which is unsubstituted or substituted at the meta position and/or the para position with a suitable substituent. Preferably, the substituent is a halogen atom, an alkyl group, an aryl or heteroaryl group, or an alkoxy group. Even more preferably, Ar is an aryl group which is substituted at the para position with a halogen atom, an alkoxy group or a heteroaryl group. Particularly preferred embodiments of the present invention include those where Ar is 4-fluorophenyl, 4-chlorophenyl, 4-methoxyphenyl or 4-(imidazol-2-yl)phenyl.

Preferably, when W is $CH_2$ or $N-R_3$, X is S, S=O, O, $N-R_3$, $N^+(O^-)-R_4$ or C=O. More preferably, when W is $CH_2$, X is O, S=O or $N-R_3$, and $R_3$ is a suitable substituent, preferably a hydrogen atom, an alkyl group, an alkylcarbonyl group, an alkoxycarbonyl group, an alkylaminocarbonyl group, a dialkylaminocarbonyl group, an alkylsulfonyl group, an arylsulfonyl group, an aminosulfonyl group or an alkylaminosulfonyl group. More preferably, $R_3$ is a hydrogen atom, a lower alkyl group, or an alkylsulfonyl group. Most preferably, when W is $CH_2$, X is O, S=O, N—H, N-($SO_2CH_3$) or N-(lower alkyl).

Alternatively, when W is $N-R_3$, X is preferably C=O and $R_3$ is preferably a hydrogen atom or an alkyl group, more preferably a lower alkyl group.

Preferably, in the above formula I-a, $R_1$ and $R_2$ are each, independently of one another, a hydrogen atom or a lower alkyl group. More preferably, $R_1$ and $R_2$ are each, independently of one another, a hydrogen atom or a methyl group.

Particularly preferred embodiments of the present invention include those compounds of the formula I-a where X is S, S=O, O, N—R or $N^+(O^-)-R_4$ and W is $CH_2$; or X is S, O or $N-R_3$ and W is C=O; or X is C=O and W is $N-R_3$; or X is $CH_2$ and W is O, S or $N-R_3$, where $R_3$ is an alkylcarbonyl group. According to these preferred embodiments of the present invention, $R_1$ and $R_2$ are preferably, independently of one another, a hydrogen atom or a methyl group, and Ar is preferably an aryl group which is unsubstituted or substituted in the para position with a suitable substituent, preferably a halogen atom, an alkoxy group or a heteroaryl group. More preferably, $R_1$ and $R_2$ are the same and Ar is an aryl group substituted in the para position with a fluorine atom, a chlorine atom, a methoxy group or an imidazolyl group. Illustrative examples of compounds according to these preferred embodiments of the present invention include, but are not limited to, 3(S)-N-hydroxy-2,2-dimethyl-4-(4-(4-(imidazol-2-yl) phenoxy) benzenesulfonyl)-tetrahydro-2H-1,4-thiazine-3-carboxamide and 3(S)-N-hydroxy-2,2-dimethyl-4-(4-((pyrid-4-yl) oxy)benzenesulfonyl)-tetrahydro-2H-1,4-thiazine-3-carboxamide.

Also, according to the preferred embodiments of the present invention where X is $N-R_3$, $R_3$ is a hydrogen atom, an alkyl group or an alkylsulfonyl group, more preferably a hydrogen atom, a methyl group or a methanesulfonyl group. Illustrative examples of compounds according to these preferred embodiments of the present invention include, but are not limited to, (R)-N-hydroxy-1-(4-(4-chlorophenoxy) benzenesulfonyl)-4-(methanesulfonyl)-piperazine-2-carboxamide, (R)-N-hydroxy-1-(4-(4-fluorophenoxy) benzenesulfonyl)-1-(methanesulfonyl)-piperazine-2-carboxamide, (R)-N-hydroxy-1-(4-(4-methoxyphenoxy) benzenesulfonyl)-4-(methanesulfonyl)-piperazine-2-carboxamide, (R)-N-hydroxy-1-(4-(4-chlorophenoxy) benzenesulfonyl)-4-methylpiperazine-2-carboxamide, (R)-N-hydroxy-1-(4-(4-fluorophenoxy)-benzenesulfonyl)-4-methylpiperazine-2-carboxamide, (R)-N-hydroxy-1-(4-(4-chlorophenoxy)benzenesulfonyl)-piperazine-2-carboxamide, and (R)-N-hydroxy-1-(4-(4-fluorophenoxy) benzenesulfonyl)-piperazine-2-carboxamide.

If the inventive compound is a base, the desired pharmaceutically acceptable salt may be prepared by any suitable method available in the art, for example, treatment of the free base with an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha-hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If the inventive compound is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include organic salts derived from amino acids, such as glycine and arginine, ammonia, primary, secondary and tertiary amines, and cyclic amines, such as piperidine, morpholine and piperazine, and inorganic salts derived from sodium, calcium, potassium, magnesium, manganese, iron, copper, zinc, aluminum and lithium.

The inventive compounds may exist as single stereoisomers (i.e., essentially free of other stereoisomers), racemates, and/or mixtures of enantiomers and/or diastereomers. All such single stereoisomers, racemates and mixtures thereof are intended to be within the scope of the present invention. Preferably, the inventive compounds are used in optically pure form.

Preferably, the hydroxamate-bearing carbon, i.e., the carbon atom designated with "*" in formula I and I-a, is in the "R" configuration when X is $CH_2$, C=O, O, $N-R_3$, or $N^+(O^-)-R_4$ and in the "S" configuration when X is S or S=O. It is understood by those skilled in the art that this designation of configuration is a consequence of the sequence rules of the Cahn-Ingold-Prelog system. When X is S=O, the sulfur atom is also preferably in the "R" configuration in relation to the preferred "S" configuration at the hydroxamate-bearing carbon atom.

As generally understood by those skilled in the art, an optically pure compound having one chiral center (i.e., one asymmetric carbon atom) is one that consists essentially of one of the two possible enantiomers (i.e., is enantiomerically pure), and an optically pure compound having more than one chiral center is one that is both diastereomerically pure and enantiomerically pure. Preferably, the compounds of the present invention are used in a form that is at least 90% optically pure, that is, a form that contains at least 90% of a single isomer (80% enantiomeric excess ("e.e.") or diastereomeric excess ("d.e.")), more preferably at least 95% (90% e.e. or d.e.), even more preferably at least 97.5% (95% e.e. or d.e.), and most preferably at least 99% (98% e.e. or d.e.).

The present invention is further directed to methods of inhibiting metalloproteinase activity, for example in mammalian tissue, by administering a compound of the formula I or I-a or a pharmaceutically acceptable prodrug thereof or a pharmaceutically acceptable salt thereof. The activity of the inventive compounds as inhibitors of metalloproteinase activity, such as the activity of MMPs (including stromelysins, collagenases, gelatinases and/or matrilysin) and/or TNF-α convertase, may be measured by any of the methods available to those skilled in the art, including in vivo and/or in vitro assays. Examples of suitable assays for activity measurements include those described in Anal. Biochem., vol. 147, p. 437 (1985), Anal. Biochem., vol. 180, p. 110 (1989), FEBS, vol. 96, p. 263 (1992) and European Patent Application No. 0 606 046.

Administration of the compounds of the formula I or I-a or their pharmaceutically acceptable prodrugs or salts may be performed according to any of the accepted modes of administration available to those skilled in the art. Illustrative examples of suitable modes of administration include oral, nasal, parenteral, topical, transdermal and rectal. Preferably, the mode of administration is oral.

The inventive compounds of the formula I and I-a and the pharmaceutically acceptable salts and prodrugs thereof may be administered as a pharmaceutical composition in any suitable pharmaceutical form recognizable to the skilled artisan. Suitable pharmaceutical forms include, but are not limited to, solid, semisolid, liquid or lyophilized formulations, such as tablets, powders, capsules, suppositories, suspensions and aerosols. Preferably, the pharmaceutical form is a tablet or capsule for oral administration. The pharmaceutical composition may also include suitable excipients, diluents, vehicles and carriers as well as other pharmaceutically active agents, depending upon the intended use.

Acceptable methods of preparing suitable pharmaceutical forms of the pharmaceutical compositions are known to those skilled in the art. For example, pharmaceutical preparations may be prepared following conventional techniques of the pharmaceutical chemist involving steps such as mixing, granulating and compressing when necessary for tablet forms, or mixing, filling and dissolving the ingredients as appropriate, to give the desired products for oral, parenteral, topical, intravaginal, intranasal, intrabronchial, intraocular, intraaural and/or rectal administration. Illustrative examples of such methods include those described in *Remington's Pharmaceutical Sciences*, 18th edition (1990).

Solid or liquid pharmaceutically acceptable carriers, diluents, vehicles or excipients may be employed in the pharmaceutical compositions. Illustrative solid carriers include starch, lactose, calcium sulphate dihydrate, terra alba, sucrose, talc, gelatin, agar, pectin, acacia, magnesium stearate and stearic acid. Illustrative liquid carriers include syrup, peanut oil, olive oil, saline solution and water. The carrier or diluent may include a suitable prolonged-release material, such as glyceryl monostearate or glyceryl distearate, alone or with a wax. When a liquid carrier is used, the preparation may be in the form of a syrup, elixir, emulsion, soft gelatin capsule, sterile injectable liquid (e.g. solution), or a nonaqueous or aqueous liquid suspension.

A dose of the pharmaceutical composition contains at least a therapeutically effective amount of the active compound (i.e., a compound of the formula I or I-a or a pharmaceutically acceptable prodrug or salt thereof) and preferably is made up of one or more pharmaceutical dosage units. An exemplary dosage unit for a mammalian host contains an amount of from 0.1 milligram up to 500 milligrams of active compound per kilogram body weight of the host, preferably 0.1 to 200 milligrams, more preferably 50 milligrams or less, and even more preferably about 10 milligrams or less, per kilogram of the host weight. The selected dose may be administered to a mammal, for example, a human patient in need of treatment mediated by inhibition of metalloproteinase activity, by any known method of administrating the dose including: topically, for example, as an ointment or cream; orally; rectally, for example, as a suppository; parenterally by injection; or continuously by intravaginal, intranasal, intrabronchial, intraaural or intraocular infusion.

The amount of the inventive compounds, salts and/or prodrugs to be administered will vary based upon a number of factors, including the specific metalloproteinase to be inhibited, the degree of inhibition desired, the characteristics of the mammalian tissue in which inhibition is desired, the metabolic stability and activity of the particular inventive compound employed, and the mode of administration. One skilled in the art may readily determine a suitable dosage according to methods known to the art. Preferably, the amount of inventive compound of the formula I or I-a administered is between 0.1 mg/kg body weight and 100 mg/kg body weight per day.

The inventive compounds, and the salts thereof and prodrugs thereof, may be prepared by employing the techniques available in the art using starting materials that are readily available. Novel and exemplary methods of preparing the inventive compounds are described below.

Preferably, the inventive compounds of the formula I-a are prepared by the novel methods of the present invention, including the general procedure shown in the following scheme.

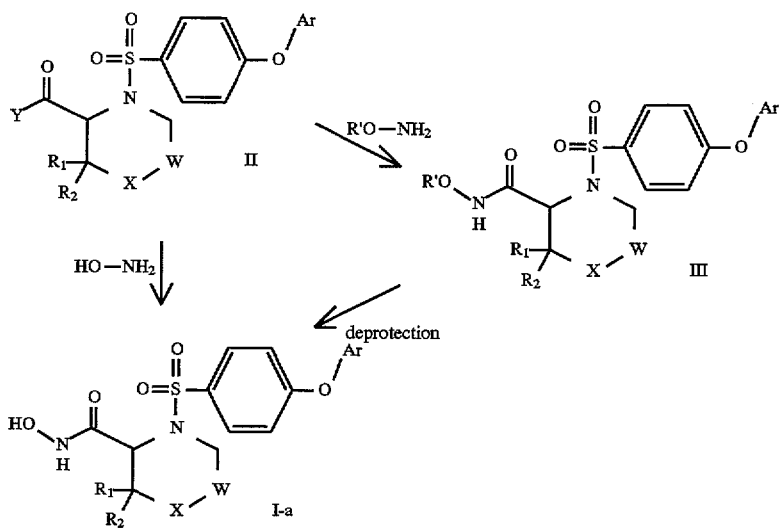

The inventive compounds of the formula I-a may be preferably prepared by reacting a compound of the formula II where Y is a hydroxy group with hydroxylamine in the presence of a suitable peptide coupling reagent. Illustrative examples of suitable coupling agents include 1,1'-carbonyldiimidazole, N-(dimethylaminopropyl)-N'-ethyl carbodiimide, benzotriazol-1-yloxy-tris(dimethylamino) phosphonium hexafluorophosphate, or propanephosphonic anhydride in an inert polar solvent, such as dimethylformamide ("DMF").

Alternatively, a compound of the formula II where Y is a halogen such as chlorine may be reacted with hydroxylamine in two-phase dichloromethane-water solvent, preferably at 0° C., to give hydroxamates of the formula I-a.

Compounds of the formula II where Y is a halogen are preferably prepared in a form that is directly useful for further reaction without isolation. For example, such compounds may be prepared by allowing compounds of the formula II where Y is a hydroxy group to react with a suitable halogenating agent, such as thionyl chloride or oxalyl chloride, preferably in the presence of a catalytic amount of dimethylformamide, and preferably in a suitable solvent such as dichloromethane at a temperature from 0° C. to room temperature.

Compounds of the formula II where Y is a hydroxy group may also be prepared by alkaline hydrolysis of the corresponding ester, such as methyl, ethyl, benzyl or t-butyl, using a suitable aqueous base, such as lithium hydroxide, preferably in a homogeneous aqueous-organic solvent mixture at a temperature from 0° C. to 25° C. Alternatively, these compounds may also be prepared by acidic hydrolysis of the corresponding ester using a suitable aqueous acid, such as hydrochloric acid in aqueous dioxane, at a suitable temperature, preferably from 50° C. to 100° C. Other methods recognizable by those skilled in the art as suitable for converting esters to acids may also be employed, such as hydrogenolysis of benzyl esters using hydrogen and palladium on carbon or acid-promoted cleavage of t-butyl esters under anhydrous conditions.

Alternatively, the coupling reactions described above may be carried out with compounds of the formula II where Y is a hydroxy group or a halogen atom and oxygen-protected compounds of hydroxylamine (i.e., where R' in formula III is a suitable protecting group known to those skilled in the art, such as benzyl, t-butyl, t-butyldimethylsilyl, or t-butyldiphenylsilyl) to give compounds of formula III. Deprotection of compounds of the formula III provides compounds of formula I-a. Suitable methods of deprotecting compounds of the formula III are known in the art; for example, as described in T. W. Greene and P. G. M. Wuts, *Protective Groups in Organic Synthesis* (1991).

Compounds of the formula I-a where W is $CH_2$ and X is N—$R_3$, in which $R_3$ is an alkyl group, may be prepared directly from compounds of the formula I-a where X is N—H, for example by treatment with a suitable alkylating agent, such as an alkyl halide or alkyl sulfonate ester, in a suitable solvent at an appropriate temperature, such as THF at a temperature from 0° C. to 50° C.

Compounds of the formula I-a where X is N—$R_3$ and $R_3$ is an alkylsulfonyl group or an arylsulfonyl group may also be prepared directly from compounds of the formula I-a where X is N—H, for example by treatment with 2 equivalents of trimethylchlorosilane in the presence of an excess of a tertiary base, such as 4-methylmorpholine, in an aprotic solvent, such as dichloromethane, at 25° C, followed by treatment with an alkylsulfonyl chloride or an arylsulfonyl chloride at a temperature from 0° C. to 25° C.

Compounds of formula II where Y is a hydroxy group and X is N—$R_3$ may be preferably prepared according to the following scheme.

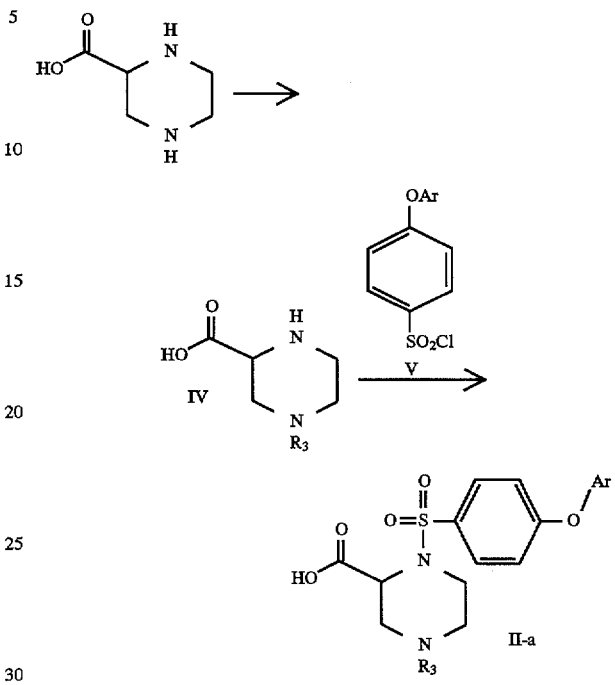

Preferably, commercially available racemic piperazine-2-carboxylic acid is allowed to react with a suitable electrophilic reagent $R_3$-Y under conditions such that the reaction takes place predominantly at the N-4 position to give compounds of the formula IV. More preferably, the reaction takes place in aqueous-organic solvent, such as acetonitrile-water, at a temperature from −20° C. to 25° C., and in the presence of excess base such as triethylamine.

For the preparation of enantiomerically pure compounds of the formula II, racemic piperazine-2-carboxylic acid may be first resolved according to known methods, such as those described in *Helv. Chim. Acta*, vol. 43, p. 888 (1960), and *Helv. Chim. Acta*, vol. 72, p. 1043 (1989).

Examples of suitable electrophilic reagents $R_3$-Y with suitable regioselectivity include BOC-ON, di-t-butyl dicarbonate, N-(benzyloxycarboxy)succinimide, and acetic anhydride. The intermediate of the formula IV is then preferably further reacted, without isolation, under the same conditions with a sulfonyl chloride of the formula V to give compounds of the formula II-a.

Alternatively, the intermediate of the formula IV may be isolated and then allowed to react with trimethylsilyl chloride and a suitable tertiary amine base, such as triethylamine or 4-methylmorpholine. Without isolation, the resulting material is then reacted with a sulfonyl chloride in a suitable solvent such as dichloromethane at 25° C. to provide, after conventional acid workup, a compound of the formula II-a.

The intermediate of the formula IV may also be prepared by heating the copper (II) complex of piperazine-2-carboxylate, prepared according to the method described in U.S. Pat. No. 4,032,639, the disclosure of which is herein incorporated by reference, with $R_3$-Y, followed by decomplexation by acidification and ion-exchange chromatography using DOWEX 50 resin.

Compounds of formula V may be preferably prepared by treatment of the corresponding Ar phenyl ether with an excess of chlorosulfonic acid in dichloromethane solution at a temperature from 0° C. to 25° C. Optionally, such as when Ar is phenyl, the aryl phenyl ether may be treated with up to 1 molar equivalent of chlorosulfonic acid, and the resulting crude sulfonic acid subsequently converted to the sulfonyl chloride with an excess of oxalyl chloride in the presence of a catalytic amount of dimethylformamide ("DMF") in dichloromethane solution.

Alternatively, compounds of the formula II-a' are first converted to the corresponding methyl esters VII by conventional methods, such as treatment with trimethylsilyl diazomethane in a suitable solvent such as methanol-dichloromethane at room temperature as shown in the following scheme.

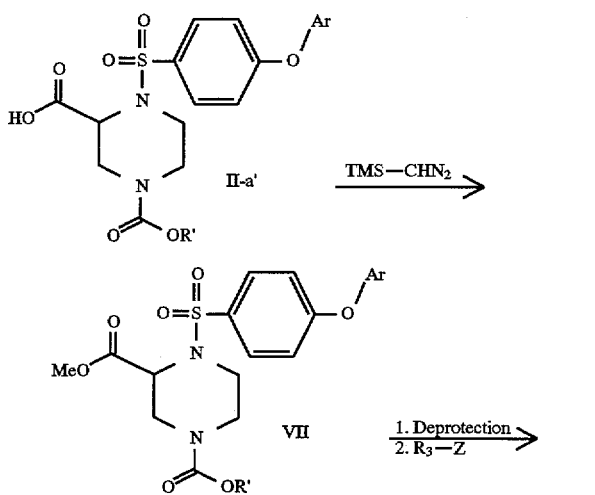

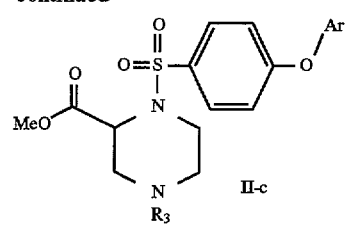

Suitable protecting groups, R', are recognizable to those skilled in the art and include, but are not limited to, t-butyl groups and benzyl groups. Removal of the protecting group by known methods provides compounds of formula II-c where X is NH. These compounds may be further reacted with reagents having the formula $R_3$-Z, wherein Z is any suitable leaving group, to give compounds of the formula II-c. Illustrative examples of suitable $R_3$-Z reagents include methanesulfonyl chloride, methyl iodide, methyl isocyanate, ethyl bromoacetate, dimethylcarbamoyl chloride, and methoxyacetic anhydride.

Compounds of the formula II where Y is a hydroxy group and X is O may be preferably prepared according to the following scheme.

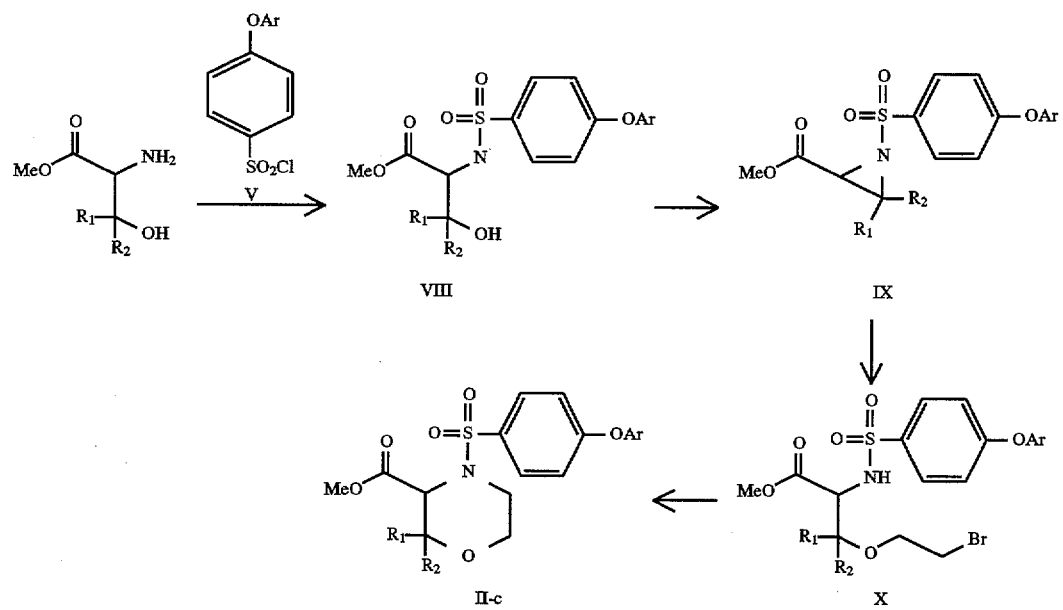

Preferably, for those compounds where $R_1$ and $R_2$ are both hydrogen, D-serine methyl ester hydrochloride is treated with an aryloxybenzenesulfonyl chloride having the formula V in the presence of a suitable tertiary amine base, such as N-methylmorpholine, in an aprotic solvent, such as DMF-dichloromethane, at 0° C. to 25° C. to provide the N-sulfonyl D-serine methyl ester having the formula VIII.

Treatment of the compound of the formula VIII with triphenylphosphine and diethyl azodicarboxylate in THF solution at 25° C. affords the aziridine having the formula IX, which upon standing in 2-bromoethanol solution in the presence of boron-trifluoride etherate at 0° C. to 25° C. gives the 2-bromoethyl ether having the formula X. Subsequent treatment of the compound having the formula X with a base such as potassium carbonate in an aprotic solvent such as DMF then provides compounds of formula II-c.

Compounds of formula II where X is S may be prepared as shown in the following scheme.

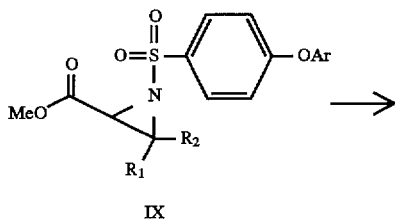

IX

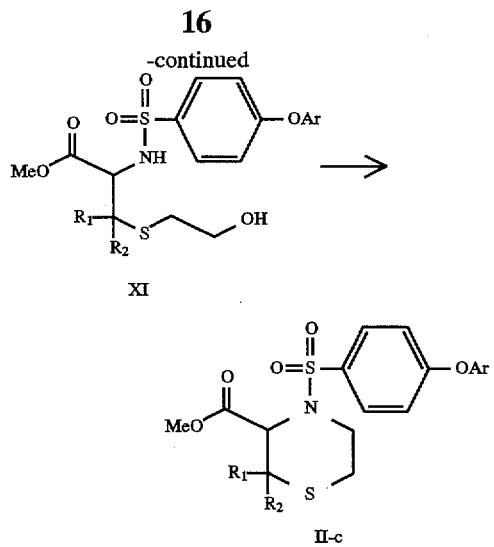

XI

II-c

The aziridine of the formula IX is preferably treated with 2-mercaptoethanol and boron trifluoride etherate in dichloromethane at 25° C. to provide the 2-hydroxyethyl sulfide having the formula XI. Cyclization of XI to II-c may then be effected with triphenylphosphine and diethylazodicarboxylate in tetrahydrofuran ("THF") solution at 25° C.

Alternatively, compounds of the formula II where X is S or S=O and $R_1$ and $R_2$ are both hydrogen may be prepared according to the following scheme.

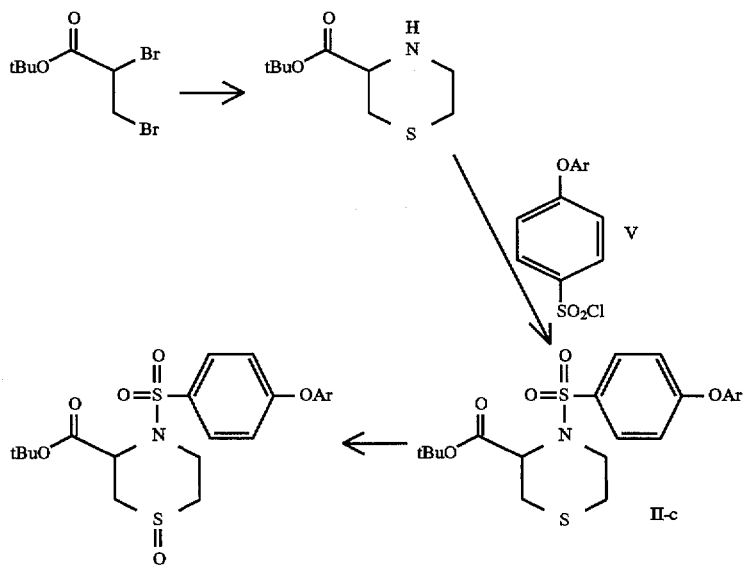

Preferably, t-butyl 2,3-dibromopropionate prepared according to *J. Perkin Trans I*, p. 1321 (1973) is treated with 2-mercaptoethylamine and triethylamine in a suitable solvent, such as a mixture of chloroform and benzene, to provide t-butyl tetrahydro-2H-1,4-thiazine-3-carboxylate, which upon reaction with a compound of the formula V under suitable conditions, such as in the presence of triethylamine in dichloromethane solution at 25° C., provides compounds of the formula II-c. Oxidation of this material with a suitable oxidizer, such as sodium perborate or m-chloroperbenzoic acid, provides the corresponding sulfoxide, preferably as a single diastereomer.

Compounds of the formula I-a where W is N—H and X is C=O may be prepared according to the following scheme.

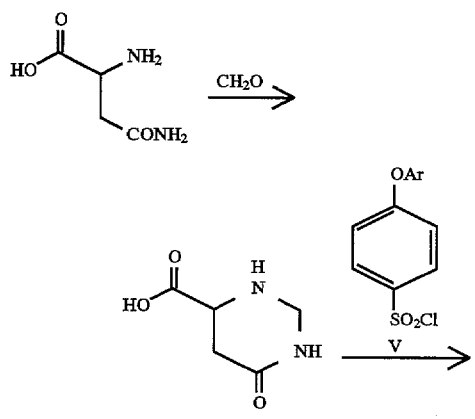

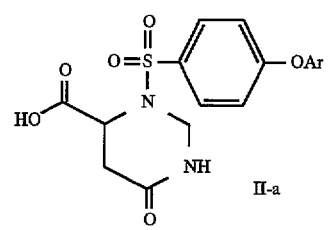

Preferably, a warm aqueous solution of D-asparagine is treated with formalin to provide, after cooling to 0° C., 6(R)-carboxytetrahydropyrimidin-4-one. Treatment of 6(R)-carboxytetrahydropyrimidin-4-one with trimethylsilylchloride in a suitable base, such as N-methylmorpholine or diisopropylethylamine, in a polar aprotic solvent, such as DMF, generates the corresponding trimethylsilyl ester. This ester may be treated, without isolation, with sulfonyl chloride V in the presence of additional base for several hours at 25° C. to provide, after aqueous work-up, a compound of the formula II-a. Alternatively, the compound of the formula II-a may be prepared directly by treating a solution of 6(R)-carboxy-tetrahydropyrimidin-4-one and a base, such as N-methyl-morpholine, in a suitable aqueous:organic mixed solvent, such as water:dioxane, with a sulfonyl chloride of the formula V at 25° C. for several hours followed by aqueous acid work-up.

Compounds of the formula I-a where W is $CH_2$, X is S or S=O and $R_1$ and $R_2$ are both methyl may be prepared according to the following scheme.

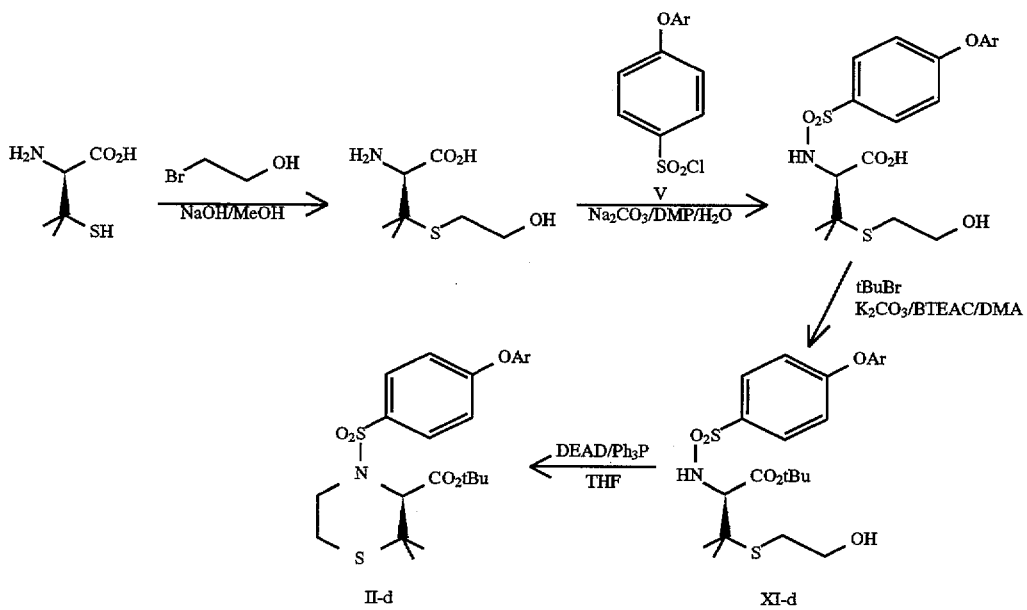

Preferably, D-penicillamine is treated with 2-bromoethanol in the presence of a base, such as sodium hydroxide, to provide a 2-hydroxyethyl sulfide intermediate. This intermediate is then reacted directly with an aryloxybenzenesulfonyl chloride of the formula V in the presence of a suitable base, such as sodium carbonate, in an appropriate solvent system, such as DMF:water to provide the N-sulfonyl derivative. The N-sulfonyl derivative is then converted to the t-butyl ester of the formula XI-d by reaction with t-butyl bromide in the presence of a suitable base, such as potassium carbonate, and a suitable catalyst, such as benzyltriethylammonium chloride ("BTEAC") in dimethylacetamide at a temperature between 50° C. and 60° C. Cyclization of the compound of the formula XI-d may be effected using triphenylphosphine and diethylazodicarboxylate ("DEAD") in a suitable solvent, such as THF, to yield a compound of the formula II-d. This compound may then be readily oxidized to the corresponding sulfoxide.

Alternatively, compounds of the formula I-a in which X is S and W is $CH_2$ may be prepared according to the following scheme.

chloride in the presence of a tertiary amine base, such as diisopropylethylamine, in an aprotic solvent, such as DMF, provides the corresponding trimethylsilyl ester, which upon reaction with 1,2-dibromoethane in the presence of DBU at 50° C. gives the intermediate tetrahydrothiazine of the formula XII. Without isolation, this intermediate is further reacted with FMOC-Cl in the presence of additional base, such as N-methyl morpholine, to provide, after aqueous acidic workup, the free carboxylic acid of the formula XIII. This acid may then be coupled to an O-protected hydroxylamine, for example where R' is t-butyldiphenylsilyl, with conventional peptide coupling reagents, such as EDC, to give the protected hydroxamate of the formula XIV. Removal of the FMOC protecting group followed by reaction with an aryloxybenzenesulfonyl chloride of the formula V in the presence of base, such as N-methyl morpholine, in a suitable solvent, such as dichloromethane, provides compounds of the formula XV. Removal of the protecting group R affords compounds of the formula I-a.

Compounds of the formula II wherein X is N—$R_3$, Y is O-t-butyl, W is $CH_2$ and $R_1$ and $R_2$ are each lower alkyl,

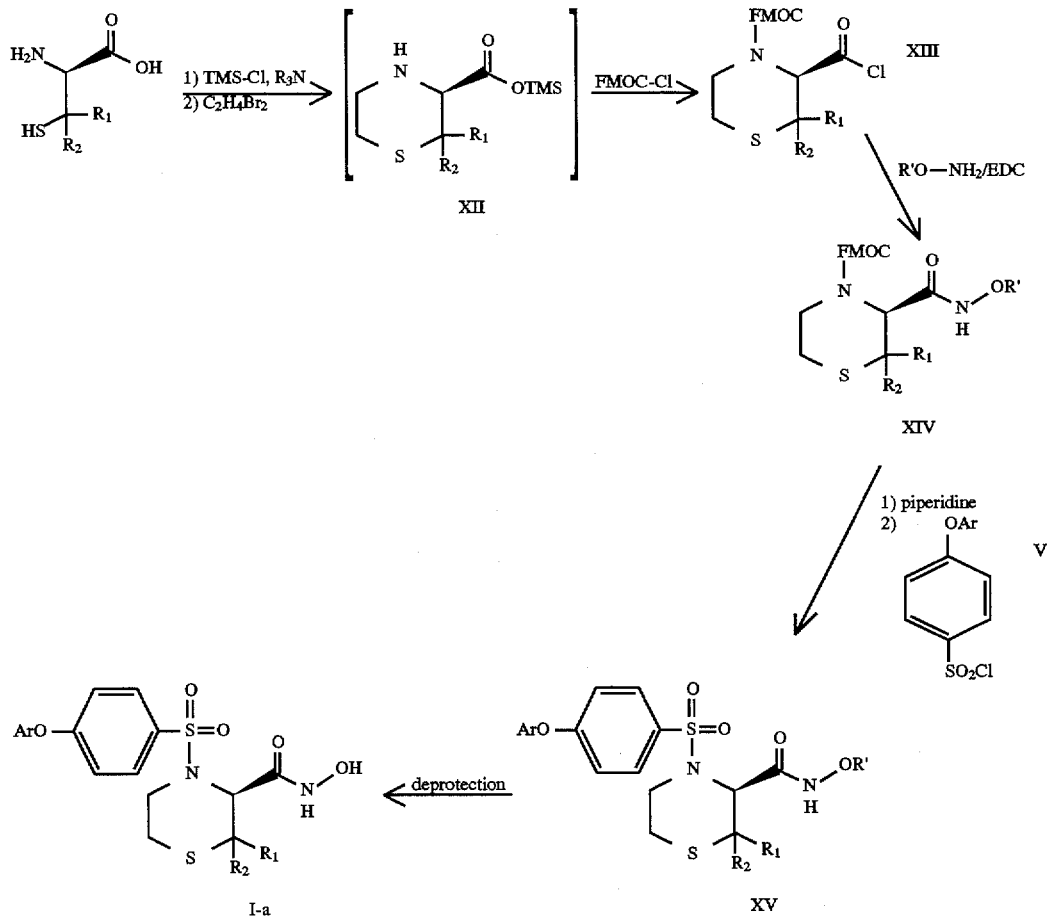

Treatment of a β-mercapto-α-amino acid, such as D-penicillamine ($R_1$ and $R_2$ are methyl), with trimethylsilyl such as methyl, may be prepared according to the following scheme.

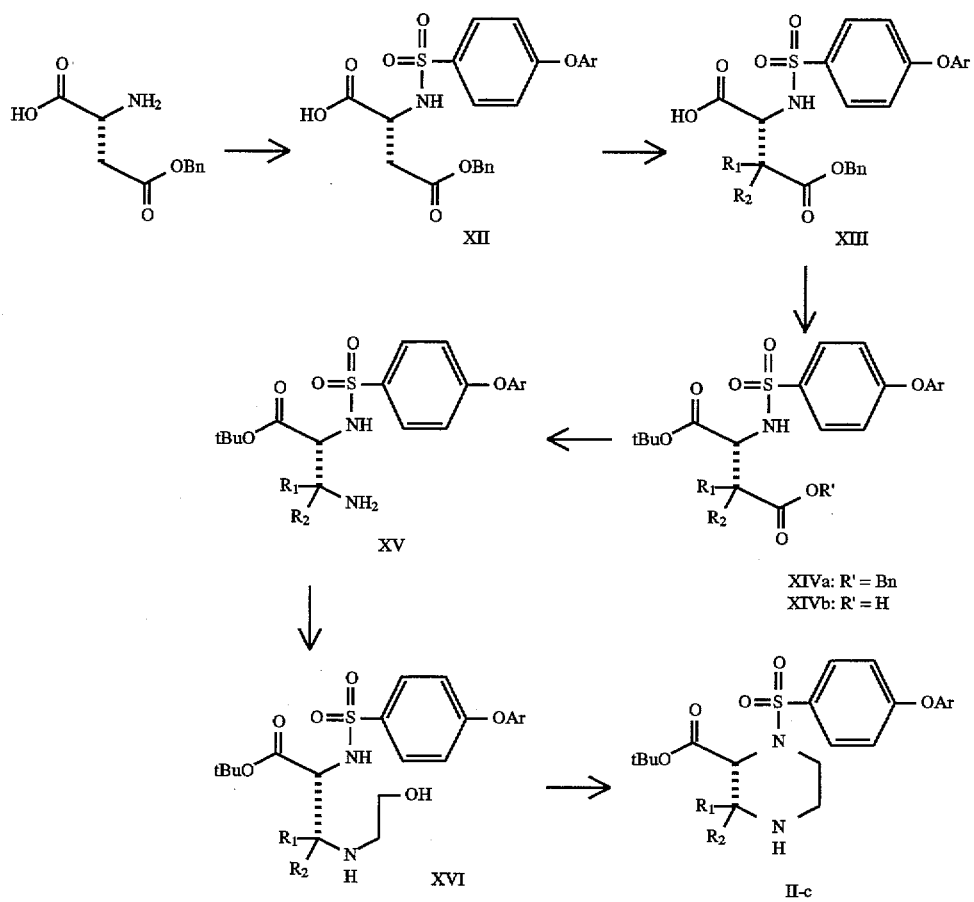

Treatment of D-aspartic acid β-benzyl ester with trimethylsilyl chloride and triethylamine in dichloromethane at 25° C. for about 1 h provides the trimethylsilyl ester, which, without isolation, is further reacted with aryl sulfonyl chloride of the formula V in the presence of additional base to provide, after conventional work-up, the corresponding sulfonamide of the formula XII. This sulfonamide is allowed to react with 3 molar equivalents of a strong base, such as lithium diisopropylamide ("LDA"), at a temperature between −78° C. and 0° C., and is then treated with 1 equivalent of an appropriate lower alkyl halide of the formula $R_1$-X, preferably at a temperature between 0° C. and −78° C. Without isolation, the reaction mixture is treated with an additional equivalent of base, and then allowed to react with a second alkyl halide of the formula $R_2$-X, where $R_1$ and $R_2$ are preferably the same but may be different, to give, after acidic work-up, a sulfonamide of the formula XIII.

Conversion of the carboxylic acid of the formula XIII to the corresponding t-butyl ester of the formula XIVa may be effected by any of the methods known to the art, such as treatment with isobutylene in the presence of catalytic sulfuric acid. Removal of the benzyl ester group by conventional means, preferably by hydrogenolysis with hydrogen gas and palladium on carbon, provides the acid of the formula XIVb. Heating of the acid at a temperature between 40° C. and 80° C. with diphenylphosphoryl azide in the presence of a suitable base, such as triethyl amine, in a mixed aqueous:organic solvent, such as water:DMF (1:4), provides an amine of the formula XV. This amine, upon treatment with ethylene oxide in isopropyl alcohol at a temperature between 25° C. and 90° C., yields an amino alcohol of the formula XVI. Treatment of this amino alcohol with triphenylphosphine and diethyl azodicarboxylate in THF solution at 25° C. provides a piperazine derivative of the formula II-c. Conversion of the piperazine derivative of the formula II-c to a compound of the formula I-a in which X is N—H or N—$R_3$ may then be performed according to the procedures described above.

Alternatively, compounds of the formula II-a in which X is N—$R_{31}$ W is $CH_2$, and $R_1$ and $R_2$ are each lower alkyl may be prepared according to the following scheme.

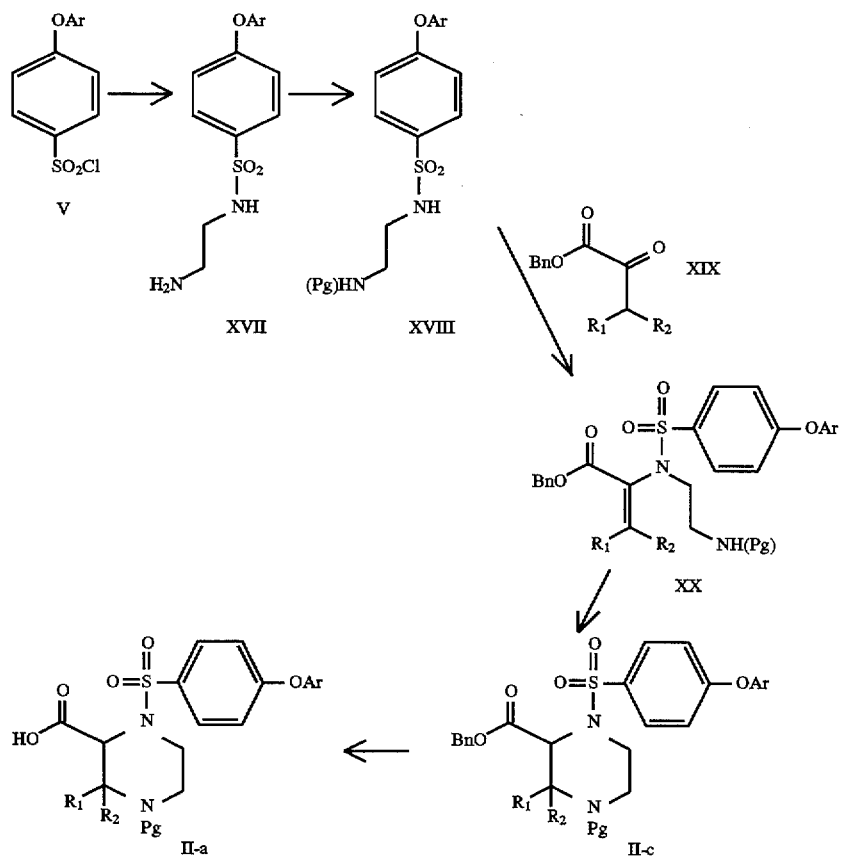

Arylsulfonyl chlorides may be converted to an amine of the formula XVII by reaction with excess ethylenediamine in THF at 0° C. The amine moiety is then protected by conventional methods ("Pg"=protecting group) to give a compound of the formula XVIII, which, upon treatment with an α-keto ester of the formula XIX in the presence of an acid catalyst, such as p-toluenesulfonic acid, provides a compound of the formula XX. Cyclization of compounds of the formula XX to the corresponding compound of the formula II-c is effected in the presence of catalytic base, such as potassium carbonate, in a suitable solvent, such as DMF. Hydrogenolysis of the benzyl ester provides a compound of the formula II-a.

Additionally, compounds of the formula II-a in which X is N—$R_3$, W is $CH_2$, and $R_1$ and $R_2$ are each lower alkyl may also be prepared according to the following scheme.

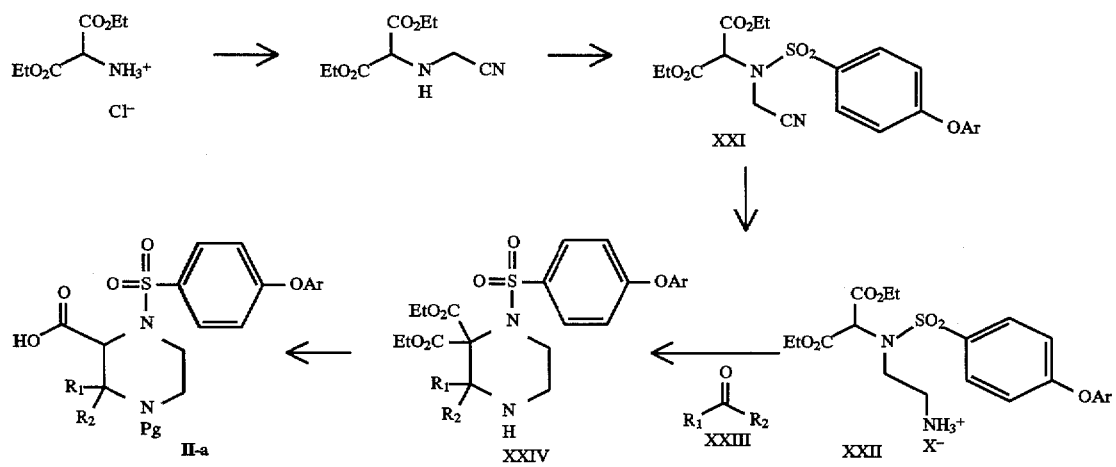

Treatment of diethyl aminomalonate with chloroacetonitrile or bromoacetonitrile in the presence of diisopropylethyl amine in ethyl alcohol provides diethyl(cyanomethyl)

aminomalonate, which is further reacted with an arylsulfonyl chloride of the formula V to give a compound of the formula XXI. The nitrile of the formula XXI may be reduced to its corresponding amine salt of the formula XXII by hydrogenation over a suitable metal catalyst, such as palladium or platinum, in the presence of acid in alcohol solution. The amine salt of the formula XXII is then allowed to react with an excess of a ketone of the formula XXIII to give a piperazine derivative of the formula XXIV. After protection of the amine function by conventional methods, hydrolysis of the ethyl esters followed by decarboxylation under acid conditions provides a compound of the formula II-a.

Other compounds of the formula I may be prepared by methods known to those skilled in the art in a manner analagous to the general procedures described above. Specific examples of methods used to prepare the inventive compounds are described below along with illustrative preferred embodiments of the inventive compounds of the formula I and I-a.

The following specific examples are intended to be illustrative of the invention and should not be construed as limiting the scope of the invention as defined by the appended claims. These examples include preferred embodiments of the inventive compounds.

EXAMPLE 1

2(R/S)-N-hydroxy-1-(4-(4-bromophenoxy)benzenesulfonyl)-4-(t-butoxycarbonyl)-piperazine-2-carboxamide To a solution of 12.45 g (50 mmol) of 4-bromobiphenyl ether in 50 mL of dichloromethane at −5° C. was added 9.9 mL (17.4 g, 150 mmol) of chlorosulfonic acid dropwise. After the addition was complete, the reaction was allowed to warm to room temperature for one hour (needed to completely convert the initially formed sulfonic acid to the sulfonyl chloride). The reaction mixture was added to cold pH 7 phosphate buffer (ca. 0.5M) and twice extracted with 50 mL of dichloromethane. The organic extracts were combined and washed with brine, dried over sodium sulfate, and concentrated. Addition of hexane to the residual syrup and re-concentration gave 13.9 g (80%) of 4-(4-bromophenoxy)benzenesulfonyl chloride as a white powder: mp 80.9° C.

A solution of 2(R/S)-piperazine-2-carboxylic acid dihydrochloride (1.06 g, 5.23 mmol) in 8 mL of 1:1 dioxane:water was brought to pH 11 with 10% aqueous sodium hydroxide and then cooled to 0° C. To this solution was added a solution of di-t-butyldicarbonate (1.37 g, 6.28 mmol) in 3 mL of dioxane, and the reaction mixture was allowed to warm slowly to room temperature overnight. The reaction mixture was then re-cooled to 0° C., and triethylamine (4.0 mL) and 4-(4-bromophenoxy)benzenesulfonyl chloride (2.00 g, 5.75 mmol, as a solution in 3 mL of dioxane) was added. The reaction mixture was stirred for 5 h at 0° C. to room temperature, and then acidified to pH 2.5 with 2N hydrochloric acid. The mixture was extracted with ethyl acetate (3×100 mL) and the combined organic layers were washed with 1N aqueous sodium hydrogen sulfate and brine, dried over sodium sulfate, and concentrated. The residue was purified by chromatography on 200 g of silica, eluting with 1:10:1 ethyl acetate:hexane:acetic acid, to give 1.07 g (38%) of 2(R/S)-1-(4-(4-bromophenoxy)benzenesulfonyl)-4-(t-butoxycarbonyl)-piperazine-2-carboxylic acid: mp 112.8° C.

To a solution of 2(R/S)-1-(4-(4-bromophenoxy)benzenesulfonyl)-4-(t-butoxycarbonyl)-piperazine-2-carboxylic acid (2.42 g, 4.47 mmol) in 15 mL of anhydrous dichloromethane at 0° C. was added O-(t-butyldimethylsilyl)hydroxylamine (998 mg, 6.71 mmol), followed by a solution of EDC methiodide (1.99 g, 6.71 mmol) in 20 mL of dichloromethane. The resulting mixture was stirred for 16 h at 0° C. to room temperature, and then concentrated in vacuo. The residue was partitioned between ethyl acetate and water, and the organic layer was washed with water, saturated aqueous sodium bicarbonate, and brine. After drying over sodium sulfate, the organic layer was concentrated, and the residue was purified by rapid filtration through a pad of silica gel, eluting with 1:1 ethyl acetate:hexane. After concentration of the filtrate, the residue was triturated with hexane, filtered, and dried under vacuum to give, in two crops, 1.78 g (61%) of 2(R/S)-N-(t-butyldimethylsilyloxy)-1-(4-(4-bromophenoxy)benzenesulfonyl)-4-(t-butoxycarbonyl)-piperazine-2-carboxamide as a white solid: mp 163.6° C.

To a solution of 2(R/S)-N-(t-butyldimethylsilyloxyl)-1-(4-(4-bromophenoxy)benzenesulfonyl)-4-(t-butoxycarbonyl)-piperazine-2-carboxamide (1.599 g, 2.38 mmol) in 8 mL of anhydrous THF was added a 1M solution of tetrabutylammonium fluoride in THF (3.6 mL). After 0.5 h, the reaction mixture was concentrated and the residue was partitioned between ethyl acetate and water. The organic layer was washed with saturated aqueous sodium bicarbonate and brine, dried over sodium sulfate, and concentrated. Trituration of the residue with t-butyl methyl ether:hexane gave a precipitate which was filtered and dried under vacuum to give 1.320 g (99%) of 2(R/S)-N-hydroxy-1-(4-(bromophenoxy)benzenesulfonyl)-4-(t-butoxycarbonyl)-piperazine-2-carboxamide: mp 112.4° C.

Anal. calc. for $C_{22}H_{26}BrN_3O_7S$: C, 47.49; H, 4.71; N, 7.55; Found: C, 47.56; H, 5.01; N, 7.42.

EXAMPLE 2

(a) 2(R/S)-N-hydroxy-1-(4-(4-bromophenoxy)benzenesulfonyl)piperazine-2-carboxamide hydrochloride 2(R/S)-N-hydroxy-1-(4-(4-bromophenoxy)benzenesulfonyl)-4-(t-butoxycarbonyl)-piperazine-2-carboxamide (999.1 mg, 1.80 mmol) was dissolved in 40 mL of 4:3:1 ethyl acetate/dichloromethane/methanol with gentle heating. The resulting clear solution was allowed to cool to room temperature, and 5 mL of 4M hydrogen chloride in dioxane was added. After 5 hours, the reaction mixture was partially concentrated under reduced pressure, and then diluted with ethyl acetate:ethyl ether. The precipitate was collected by filtration, washed with ethyl acetate and ethyl ether, and dried under vacuum to give 548.8 mg (62%) of 2(R/S)-N-hydroxy-1-(4-(4-bromophenoxy)benzenesulfonyl)-piperazine-2-carboxamide hydrochloride as a white solid: mp 186.6° C.

Anal. calc. for $C_{17}H_{19}ClBrN_3O_5S$: C, 41.43; H, 3.89; N, 8.53; Found: C, 41.47; H, 3.96; N, 8.38.

The following compound was prepared in a similar manner: (b) 2(R/S)-N-hydroxy-1-(4-phenoxybenzenesulfonyl)-piperazine-2-carboxamide: mp 160.4° C.;

Anal. calc. for $C_{17}H_{19}N_3O_5S$: C, 54.10; H, 5.07; N, 11.13; S, 8.50; Found: C, 54.04; H, 5.09; N, 11.06; S, 8.44.

EXAMPLE 3

(a) 2(R/S)-N-hydroxy-1-(4-(4-chlorophenoxy)benzenesulfonyl)-4-(N-methylcarbamoyl)-piperazine-2-carboxamide To a suspension of 1.20 g of 2(R/S)-4-(benzyloxycarbonyl)piperazine-2-carboxylic acid (obtained according to the method of M. E. Freed and J. R. Potoski, U.S. Pat. No. 4,032,639 (1977), the disclosure of which is herein incorporated by reference) in dichloromethane (2.5 mL) at 0° C. was added 0.63 mL of trimethylsilyl chloride. After 10 min, triethylamine (1.55 mL) was added, followed by addition of 1.37 g of 4-(4-chlorophenoxy) benzenesulfonyl chloride (mp 60.6° C., prepared from 4-chlorodiphenyl ether in a manner similar to that described in Example 1). After 3 h, the mixture was partitioned between dichloromethane and pH 4 citrate buffer. The organic layer was washed with water, dried over sodium sulfate, and concentrated. The residue was purified by chromatography, eluting with 0.5% acetic acid in 95:5 dichloromethane/ethanol, to provide 2.05 g (85%) of 2(R/S)-1-(4-(4-chlorophenoxy)benzenesulfonyl)-4-(benzyloxycarbonyl)-piperazine-2-carboxylic acid: mp 104.2° C.

Anal. calc. for $C_{25}H_{23}ClN_2O_7S$: C, 56.55; H, 4.37; N, 5.28; S, 6.04; Found: C, 56.65; H, 4.41; N, 5.22; S, 6.10.

A solution of 2(R/S)-1-(4-(4-chlorophenoxy) benzenesulfonyl)-4-(benzyloxycarbonyl)-piperazine-2-carboxylic acid (2.21 g) in 18:1:1 ethanol:ethyl acetate:water was hydrogenated at 1 atm over 10% Pd/C (0.22 g) for 1 day. The catalyst was removed by filtration and the solution concentrated to give 2(R/S)-1-(4-(4-chlorophenoxy) benzenesulfonyl)-piperazine-2-carboxylic acid of ca. 95% purity, which was used without further purification.

To a solution of 2(R/S)-1-(4-(4-chlorophenoxy) benzenesulfonyl)-piperazine-2-carboxylic acid (0.987 g) and triethylamine (0.41 mL) in 20 mL of anhydrous DMF was added methyl isocyanate (0.16 mL). After 6 h, the reaction was partitioned between (dichloromethane and 1N sodium bisulfate. The aqueous layer was extracted twice more with dichloromethane, and the combined organic layers were dried (sodium sulfate) and concentrated. The residue was purified by chromatography, eluting with 85:15 dichloromethane:ethanol containing 0.5% acetic acid, to provide 0.918 g (81%) of 2(R/S)-1-(4-(4-chlorophenoxy) benzenesulfonyl)-4-(N-methylcarbamoyl)-piperazine-2-carboxylic acid: mp 212.7° C.

Anal. calc. for $C_{19}H_{20}ClN_3O_6S$: C, 50.27; H, 4.44; N, 9.26; S, 7.06; Found: C, 50.56; H, 4.40; N, 9.38; S, 6.93.

To a solution of O-(t-butyldimethylsilyl)hydroxylamine (0.282 g) in 12 mL of 5:1 dichloromethane:DMF at 0° C. was added 0.580 g of 1-(4-(4-chlorophenoxy) benzenesulfonyl)-4-(N-methylcarbamoyl)-2R/S-piperazinecarboxylic acid followed by EDC hydrochloride (0.294 g) and the reaction mixture was stirred for 15 min at 0° C. and then allowed to warm to room temperature. After 1.5 h, the reaction was partitioned between ethyl acetate and aqueous sodium bicarbonate. The organic layer was washed with water and brine, dried over sodium sulfate, and concentrated. The residue was crystallized by slow evaporation from dichloromethane/t-butyl methyl ether/isooctane to provide 0.643 g (86%) of 2(R/S)-N-(t-butyldimethylsilyloxy)-1-(4-(4-chlorophenoxy)benzenesulfonyl)-4-(N-methylcarbamoyl)-piperazine-2-carboxamide as a white solid: mp 171.0° C.

Anal. calc. for $C_{25}H_{35}ClN_4O_6SSi$: C, 51.49; H, 6.05; N, 9.61; S, 5.50; Found: C, 51.59; H, 6.06; N, 9.67; S, 5.58.

To a solution of 2(R/S)-N-(t-butyldimethylsilyloxy)-1-(4-(4-chlorophenoxy)benzenesulfonyl)-4-(N-methylcarbamoyl)-piperazine-2-carboxamide in 20 mL of methanol at 25° C. was added 0.5 mL of trifluoroacetic acid. After 30 min, 20 mL of toluene was added and the solution was concentrated. The residue was recrystallized from (dichloromethane/t-butyl methyl ether/isooctane to give 781 mg (99%) of 2(R/S)-N-hydroxy-1-(4-(4-chlorophenoxy)-benzenesulfonyl)-4-(N-methylcarbomoyl)-piperazine-2-carboxamide as a white solid: mp 133.2° C.

Anal. calc. for $C_{19}H_{21}ClN_4O_6S$: C, 48.66; A, 4.51; N; 11.95; S, 6.84; Found C, 48.74; H, 4.53; N; 11.90; S, 6.91.

The following compounds can be prepared in a similar manner:

(b) 2(R)-N-hydroxy-1-(4-(4-fluorophenoxy) benzenesulfonyl)-4-(N-methylcarbamoyl)-piperazine-2-carboxamide;

(c) 2(R)-N-hydroxy-1-(4-(4-methoxyphenoxy) benzenesulfonyl)-4-(N-methylcarbamoyl)-piperazine-2-carboxamide; and (d) 2(R/S)-N-hydroxy-1-(4-(4-chlorophenoxy) benzenesulfonyl)-4-(N-isopropylcarbamoyl)-piperazine-2-carboxamide.

EXAMPLE 4

(a) 2(R/S)-N-hydroxy-1-(4-phenoxybenzenesulfonyl)-4-acetylpiperazine-2-carboxamide To a stirred solution of 42.5 g (0.25 mol) of phenyl ether in 200 mL of dichloromethane at −20° C. under argon was slowly added 23.3 g (0.20 mol) of chlorosulfonic acid. After the addition was complete, the reaction was allowed to slowly warm to room temperature. After 16 h, 150 mL of isooctane was added and the solution was concentrated to an oily residue. Redissolution in 200 mL of 1:3 dichloromethane/isooctane and reconcentration with cooling to about 100 mL gave a solid. The supernatant was decanted, and the solid triturated with additional isooctane and then dried in vacuo to give 55.2 g of crude 4-phenoxybenzene sulfonic acid. The crude acid was dissolved in 200 mL of dichloromethane, and 34 g (0.25 mol) of oxalyl chloride was added, followed by 2.5 mL of DMF. After 2 days, the reaction solution was poured into 200 mL of ice water, and extracted with 400 mL of hexane. The organic layer was washed with 100 mL of water and 100 mL of brine, dried over magnesium sulfate, and concentrated. Recrystallization of the residue from dichloromethane/ isooctane gave 38.5 g of 4-phenoxybenzenesulfonyl chloride as a white solid: mp 41.5° C.

To a stirred solution of 2(R/S)-piperazine-2-carboxylic acid (1.30 g, 10.0 mmol) and triethylamine (3.6 mL) in 25 mL of 2:2:1 dioxane/water/acetronitrile at −20° C. was added dropwise 1.13 mL (1.22 g, 12.0 mmol) of acetic anhydride. After 2 h at −20° C., an additional 1.5 mL of triethylamine was added, followed by 2.69 g (10 mmol) of 4-phenoxybenzenesulfonyl chloride. The reaction mixture was allowed to warm slowly to room temperature. After 18 h, the reaction was partitioned between 100 mL of 0.5N potassium dihydrogen phosphate and 100 mL of ethyl acetate. The aqueous layer was acidified with 10 mL of 2M sulfuric acid, and extracted with an additional 100 mL of ethyl acetate. The combined organic layers were dried over sodium sulfate and concentrated. The residue was dissolved in 100 mL of 1:1 toluene/methanol, and trimethylsilyldiazomethane (2M solution in hexane) was added dropwise until the yellow color no longer dissipated (about 15 mL). After addition of 2 drops of acetic acid to consume excess trimethylsilyl-diazomethane, the solution was concentrated and the residue was purified by chromatography on 150 g of silica gel, eluting with a 80% ethyl acetate/hexane to ethyl acetate gradient. Concentration of the product-containing fractions gave an oil which solidified upon trituration with t-butyl methyl ether/hexane to give 1.86 g (44%) of methyl 2(R/S)-1-(4-phenoxybenzenesulfonyl)-4-acetyl-piperazine-2-carboxylate: mp 118° C.

Anal. calc. for $C_{20}H_{22}N_2O_6S$: C, 57.41; H, 5.30; N, 6.69; S, 7.66; Found: C, 57.38; H, 5.29; N, 6.75; S, 7.72.

To a solution of methyl 2(R/S)-1-(4-phenoxybenzenesulfonyl)-4-acetyl-piperazine-2-carboxylate (1.672 g) in 12 mL of THF and 6 mL of methanol was added in a dropwise manner 4 mL of 2N aqueous lithium hydroxide. After 1 h, the reaction solution was partitioned between 100 mL of ethyl acetate and 25 mL of 1N aqueous sodium bisulfate. The organic layer was washed with brine, dried over sodium sulfate, and concentrated. The residue was triturated with t-butyl methyl ether and filtered to give 1.544 g (96%) of 2(R/S)-1-(4-phenoxybenzenesulfonyl)-4-acetyl-piperazine-2-carboxylic acid as a white solid: mp 213° C.

Anal. calc. for $C_{19}H_{20}N_2O_6S$: C, 56.43; H, 4.98; N, 6.93; S, 7.93; Found: C, 56.50; H, 4.96; N, 6.90; S, 8.01.

To a solution of O-(t-butyldimethylsilyl)hydroxylamine (0.575 g) in 13 mL of dichloromethane at 0° C. was added 1.212 g of 2 (R/S)-1-(4-phenoxybenzenesulfonyl)-4-acetyl-piperazine-2-carboxylic acid. To this mixture was added 2.0 mL of DMF, resulting in a clear solution. After about 3 min, EDC hydrochloride (0.634 g) was added in one portion, and the reaction was stirred for 15 min at 0° C. and then allowed to warm to room temperature. After 2 h, the reaction was partitioned between 100 mL of 3:1 ethyl acetate/hexane and 50 mL of water. The organic layer was washed with saturated aqueous sodium bicarbonate, 1N aqueous sodium bisulfate, and pH 7 phosphate buffer/brine, dried and concentrated. Trituration of the residue with t-butyl methyl ether/hexane and filtration gave 1.351 g (84%) of 2(R/S)-N-(t-butyldimethylsilyloxy)-1-(4-phenoxybenzenesulfonyl)-4-acetyl-piperazine-2-carboxamide as a white solid: mp 146° C.

Anal. calc. for $C_{24}H_{35}N_2O_6SSi$: C, 56.26; H, 6.61; N, 7.87; S, 6.01; Found: C, 56.33; H, 6.66; N, 7.94; S, 6.09.

To a solution of 2(R/S)-N-(t-butyldimethylsilyloxy)-1-(4-phenoxybenzenesulfonyl)-4-acetyl-piperazine-2-carboxamide (1.200 g, 2.25 mmol) in 20 mL of methanol at 25° C. was added 0.5 mL of trifluoroacetic acid. After 1 h, 20 mL of toluene was added and the solution was concentrated. The residue was recrystallized from dichloromethane/t-butyl methyl ether to give 850 mg (84%) of 2(R/S)-N-hydroxy-1-(4-phenoxybenzenesulfonyl)-4-acetyl-piperazine-2-carboxamide as a white solid: mp 171° C. (decomp).

Anal. calc. for $C_{19}H_{21}N_3O_6S \cdot 0.25\ C_5H_{12}O$ (t-BuOMe) •0.25 $H_2O$: C, 54.63; H, 5.55; N, 9.44; S, 7.20; Found: C, 54.62; H, 5.45; N; 9.38; S, 7.20.

The following compounds can be prepared in a similar manner from enantiomerically pure 2(R)-piperazine-2-carboxylate:

(b) 2(R)-N-hydroxy-1-(4-(4-chlorophenoxy) benzenesulfonyl)-4-acetyl-piperazine-2-carboxamide;

(c) 2(R)-N-hydroxy-1-(4-phenoxybenzenesulfonyl)-4-(methoxyacetyl)-piperazine-2-carboxamide;

(d) 2(R)-N-hydroxy-1-(4-phenoxybenzenesulfonyl)-4-(isobutyryl)-niperazine-2-carboxamide;

(e) 2(R)-N-hydroxy-1-(4-(pyrid-4-yl) oxybenzenesulfonyl)-4-acetylpiperazine-2-carboxamide;

(f) 2(R)-N-hydroxy-1-(4-(4-fluorophenoxy) benzenesulfonyl)-4-acetyl-piperazine-2-carboxamide; and (g) 2(R)-N-hydroxy-1-(4-(4-chlorophenoxy) benzenesulfonyl)-4-(dimethylaminoacetyl)-piperazine-2-carboxamide.

EXAMPLE 5

(a) 2(R)-N-hydroxy-1-(4-(4-chlorophenoxy) benzenesulfonyl)morpholine-2-carboxamide To mixture of D-serine methyl ester hydrochloride (11.20 g) and N-methylmorpholine (16.5 mL) in 385 mL of 10:1 dichloromethane DMF at –10° C. was added, in portions over a 2 h period, 18.18 g of 4-(4-chlorophenoxy) benzenesulfonyl chloride. The mixture was stirred an additional 2.5 h at –10° C., and then partitioned between 1M aqueous sodium bisulfate (200 mL) and 4:1 ethyl acetate-:hexane (400 mL). The aqueous layer was extracted with additional ethyl acetate:hexane (200 mL) and the combined organic layers were washed with water, 1M aqueous sodium bisulfate, saturated aqueous sodium bicarbonate, and brine. After drying over sodium sulfate, the solution was concentrated almost to dryness, and the residue was crystallized from t-butyl methyl ether:dichloromethane:isooctane to give two crops of 18.09 g and 3.20 g. Total yield of N-(4-(4-chlorophenoxy)benzenesulfonyl)-D-serine methyl ester was 21.29 g: mp 103.9° C.

To a stirred solution of N-(4-(4-chlorophenoxy) benzenesulfonyl)-D-serine methyl ester (8.3 g) and triphenyl phosphine (6.79 g) in 150 mL of THF was added diethyl azodicarboxylate (4.07 mL) in 2.5 mL THF. After 18 h, the reaction was partitioned between 1:1 ethyl acetate:hexane and water, and the organic layer was washed with brine, dried over sodium sulfate, and concentrated. Chromatography of the residue (20% ethyl acetate:hexane) provided 7.05 g (89%) of methyl 2(R)-1-(4-(4-chlorophenoxy) benzenesulfonyl)aziridine-2-carboxylate as a thick syrup.

To a stirred solution of methyl 2(R)-1-(4-(4-chlorophenoxy)benzenesulfonyl)aziridine-2-carboxylate (6.81 g) in 13 mL of 2-bromoethanol at 0° C. was added dropwise 1.85 mL of boron trifluoride etherate. The reaction was stirred for 30 min at 0° C. and for 6 h at room temperature, and then partitioned between 200 mL of 0.1N pH 7 phosphate buffer and 250 mL of 2:1 ethyl acetate:hexane. The organic layer was washed with water and brine, dried over sodium sulfate, and concentrated. Recrystallization of the residue from t-butyl methyl ether/isooctane gave 3.69 g of a slightly impure solid, which was again recrystallized from t-butyl methyl ether/isooctane to yield 2.35 g of fine white needles. The combined filtrates were concentrated and the residue was chromatographed on 150 g of silica gel with 40% to 50% t-butyl methyl ether in hexane. The product-containing fractions were partially concentrated to ca. 50 mL volume, and the crystalline solid isolated by filtration to provide an additional 1.11 g of product. Total yield of N-(4-(4-chlorophenoxy)benzenesulfonyl)-O-(2-bromoethyl)-D-serine methyl ester was 4.36 g (51%): mp 98° C.

To a solution of N-(4-(4-chlorophenoxy)benzenesulfonyl) -O-(2-bromoethyl)-D-serine methyl ester (3.94 g) in 40 mL of anhydrous DMF at 0° C. was added 4.0 g of powdered potassium carbonate. After the addition, the ice bath was removed, and the mixture was stirred vigorously as the reaction was allowed to warm to room temperature. After 1 h, the mixture was partitioned between 200 mL of water and 200 mL of 1:1 ethyl acetate:hexane. The organic layer was washed with 200 mL of 0.1N pH 7 phosphate buffer, 50 mL of water, and 50 mL of brine, dried over sodium sulfate, and concentrated. The resulting thick syrup (3.86 g) was dissolved in 60 mL of 4:1:1 dioxane:methanol:water at 0° C. and 10 mL of 2N aqueous lithium hydroxide was added. The mixture was stirred for 30 min at 0° C. and then allowed to warm to room temperature. After an additional hour, the reaction was partitioned between 250 mL of 2:1 ethyl acetate:hexane and 100 mL of 0.5N aqueous sodium bisulfate. The aqueous layer was extracted with an additional 50 mL of ethyl acetate:hexane, and the combined organic layers were washed with brine, dried over sodium sulfate, and concentrated. The residue was chromatographed on 150 g of silica with 70% ethyl acetate:hexane containing 0.5% acetic acid. The product-containing fractions were concentrated to provide 2.98 g (94%) of 2(R)-1-(4-(4-chlorophenoxy)benzenesulfonyl)-morpholine-2-carboxylic acid as a syrup which solidified on standing: mp 161.8° C.

To a solution of 2(R)-1-(4-(4-chlorophenoxy)benzenesulfonyl)morpholine-2-carboxylic acid (3.06 g) in 35 mL of 6:1 dichloromethane:DMF at 0° C. was added O-(t-butyldimethysilyl)hydroxylamine (1.47 g) followed by EDC hydrochloride (1.77 g). The solution was stirred for 30 min at 0° C. and then allowed to warm to room temperature. After 2 h, the reaction was partitioned between 150 mL of 1:1 ethyl acetate:hexane and 100 mL of water. The organic layer was washed with cold 0.1N aqueous sodium bisulfate (25 mL), 0.1N aqueous sodium bicarbonate (25 mL), and brine, dried over sodium sulfate, and concentrated to an oil which solidified upon standing. Trituration with hexane and filtration gave 3.46 g (85%) of 2(R)-N-(t-butyldimethylsilyloxy)-1-(4-(4-chlorophenoxy)benzenesulfonyl)-morpholine-2-carboxamide as a white solid: mp 129.6° C.

To a suspension of 2(R)-N-(t-butyldimethylsilyloxy)-1-(4-(4-chlorophenoxy)benzenesulfonyl)-morpholine-2-carboxamide (3.35 g) in 25 mL of methanol at 25° C. was added 0.3 mL of trifluoroacetic acid. After 1 h, 20 mL of toluene was added and the solution was concentrated to a volume of about 10 mL. Upon addition of an additional 10 mL of toluene, a solid precipitated. After a few minutes, 20 mL of hexane was added and the solid was collected by filtration and dried in vacuo to give 2.65 g (95%) of 2(R)-N-hydroxy-1-(4-(4-chlorophenoxy)benzenesulfonyl)-morpholine-2-carboxamide•0.33 toluene as a white solid: mp 104° C.

Anal. calc. for $C_{17}H_{17}ClN_2O_6S$•0.33 $C_7H_8$: C, 52.32; H, 4.47; N, 6.32; Cl, 8.00; S, 7.23; Found: C, 52.31; H, 4.47; N, 6.26; Cl, 7.97; S, 7.38.

The following compounds can be prepared in similar manner:

(b) 2(R)-N-hydroxy-1-(4-phenoxybenzenesulfonyl)-morpholine-2-carboxamide;

(c) 2(R)-N-hydroxy-1-(4-(4-methoxyphenoxy)benzenesulfonyl)morpholine-2-carboxamide;

(d) 2(R)-N-hydroxy-1-(4-(pyrid-4-yl)oxybenzenesulfonyl)morpholine-2-carboxamide;

(e) 2(R)-N-hydroxy-1-(4-(4-fluorophenoxy)benzenesulfonyl)morpholine-2-carboxamide; and (f) 2(R)-N-hydroxy-1-(4-(4-(imidazol-2-yl)phenoxy)benzenesulfonyl)-morpholine-2-carboxamide.

EXAMPLE 6

(a) 2(R)-N-hydroxy-1-(4-(4-chlorophenoxy)benzenesulfonyl)-4-(t-butoxycarbonyl)-piperazine-2-carboxamide To a solution of 2(R)-piperazine-2-carboxylic acid (1.30 g) and triethylamine (3.50 mL) in 25 mL of 3:2 acetonitrile:water at −15° C. was added BOC-ON (2.70 g) in one portion. The mixture was allowed to warm slowly to 25° C. overnight, and then concentrated to a volume of ca. 10 mL. The resulting mixture was partitioned between 25 mL of water and 50 mL of 4:1 ethyl acetate:hexane. The aqueous layer was further washed with dichloromethane (3×10 mL) and then concentrated. The semi-solid residue was triturated with ethanol and filtered to give 1.18 g of 2(R)-4-(t-butoxycarbonyl)piperazine-2-carboxylate. Concentration of the filtrate gave a second crop of 0.58 g; total yield of 2(R)-4-(t-butoxycarbonyl)piperazine-2-carboxylic acid was 1.76 g (76%).

To a stirred suspension of 2(R)-4-(t-butoxycarbonyl)piperazine-2-carboxylic acid (4.62 g) and N-methylmorpholine (5.5 mL) in 90 mL of 2:1 dichloromethane:DMF was added dropwise trimethylsilyl chloride (2.79 mL) with cooling in a 15° C. water bath. After 1 h, diisopropylethylamine (3.5 mL) was added and the mixture was stirred for another hour, at which point little solid remained. Additional trimethylsilyl chloride (0.20 mL) was added, and after 30 min, the reaction was a homogeneous solution, and 4-(4-chlorophenoxy)benzenesulfonyl chloride (6.67 g) was added in one portion. The reaction was stirred for 2 h, and then quenched with ca. 10 mL of water. After 30 min, the mixture was partitioned between 300 mL of 2:1 ethyl acetate:hexane and 100 mL of 0.5N aqueous sodium bisulfate. The organic layer was washed with 100 mL each of 0.2N and 0.05N sodium bisulfate and with 50 mL of brine, dried (sodium sulfate), and concentrated. The residue was purified by chromatography on 200 g of silica, eluting with a gradient of 30% to 40% to 50% ethyl acetate:hexane containing 0.5% acetic acid, to give 9.33 g of 2(R)-4-(t-butoxycarbonyl)-1-(4-(4-chlorophenoxy)benzenesulfonyl)-piperazine-2-carboxylic acid as a solid foam containing traces of solvent.

To a solution of 2(R)-4-(t-butoxycarbonyl)-1-(4-(4-chlorophenoxy)benzenesulfonyl)-piperazine-2-carboxylic acid (995 mg) in 12 mL of dichloromethane at 0° C. was added O-(t-butyldimethylsilyl)hydroxylamine (430 mg) followed by EDC hydrochloride (460 mg). After 20 min, the reaction was allowed to warm to 25° C. After 2 h, the reaction was partitioned between water and 1:1 ethyl acetate:hexane. The organic layer was washed with water and cold 0.1N aqueous sodium bisulfate, and finally with pH 7 phosphate buffer/brine. The organic layer was dried over sodium sulfate, and concentrated to a solid. Dissolution in dichloromethane, dilution with isooctane, and partial concentration gave a heavy precipitate, which upon filtration and drying provided 1.107 g (88%) of 2(R)-N-(t-butyldimethylsilyloxy)-4-(t-butoxycarbonyl)-1-(4-(4-chlorophenoxy)benzenesulfonyl)-piperazine-2-carboxamide: mp 181.6° C.

Anal. calc for $C_{28}H_{40}ClN_3O_7SSi$: C, 53.70; H, 6.44; N, 6.71; S, 5.12; Found: C, 53.79; H, 6.46; N. 6.72; S, 5.19.

To a solution of 2(R)-N-(t-butyldimethylsilyloxy)-4-(t-butoxycarbonyl)-1-(4-(4-chlorophenoxy)benzenesulfonyl)-piperazine-2-carboxamide (100 mg) in methanol (4 mL) was added TFA (0.2 mL). After 1 h, toluene (20 mL) was added and the solution was concentrated to a solid residue, which was recrystallized from methanol to give 48 mg of 2(R)-N-hydroxy-1-(4-(4-chlorophenoxy)benzenesulfonyl)-4-(t-butoxycarbonyl)-piperazine-2-carbonxamide as fine white needles: mp 94.6° C.

The following compounds were prepared in a similar manner:

(b) 2(R)-N-hydroxy-1-(4-(4-fluorophenoxy)benzenesulfonyl)-4-(t-butoxycarbonyl)-piperazine-2-carboxamide: mp 151.2° C.;

(c) 2(R/S)-N-hydroxy-1-(4-(4-cyanophenoxy)benzenesulfonyl)-4-(t-butoxycarbonyl)-piperazine-2-carboxamide: mp 131.3° C.; and (d) 2(R/S)-N-hydroxy-1-(4-(pyrid-2-yl)oxybenzenesulfonyl)-4-(t-butoxycarbonyl)-piperazine-2-carboxamide: mp 133.5° C.;

Anal. calc. for $C_{21}H_{26}N_4O_7S$: C, 52.71; H, 5.48; N, 11.71; S, 6.70; Found: C, 52.54; H, 5.48; N, 11.61; S, 6.75.

EXAMPLE 7

(a) 2(R)-N-hydroxy-1-(4-(4-chlorophenoxy)benzenesulfonyl)piperazine-2-carboxamide hydrochloride To a solution of 2(R)-N-(t-butyldimethylsilyloxy)-4-(t-butoxycarbonyl)-1-(4-(4-chlorophenoxy)benzenesulfonyl)-piperazine-2-carboxamide (313 mg) in 7 mL of 6:1 dichloromethane:methanol was added 2.0 mL of 4M HCl in dioxane. After 1 h, the solution was partially concentrated to ca. 2 mL, diluted with 5 mL of ethyl acetate, and reconcentrated to near dryness. The residue was triturated with ethyl acetate, filtered, and dried in vacuo to provide 198 mg (88%) of 2(R)-N-hydroxy-1-(4-(4-chlorophenoxy)benzenesulfonyl)-piperazine-2-carboxamide hydrochloride as a white solid: mp 169° C.

Anal. calc. for $C_{17}H_{19}Cl_2N_3O_5S$: C, 45.54; H, 4.27; N, 9.37; Cl, 15.82; S, 7.15; Found: C, 45.59; H, 4.25; N, 9.20; Cl, 15.66; S, 7.02.

The following compound was prepared in a similar manner:

(b) 2(R)-N-hydroxy-1-(4-(4-fluorophenoxy)benzenesulfonyl)piperazine-2-carboxamide hydrochloride: mp 150.8° C.

The following compounds can be prepared in a similar manner:

(c) $^2$(R)-N-hydroxy-1-(4-(4-methoxyphenoxy)benzenesulfonyl)piperazine-2-carboxamide hydrochloride;

(d) $^2$(R)-N-hydroxy-1-(4-(4-methylphenoxy)benzenesulfonyl)piperazine-2-carboxamide hydrochloride; and (e) 2(R)-N-hydroxy-1-(4-(pyrazol-3-yl)benzenesulfonyl)-piperazine-2-carboxamide hydrochloride.

EXAMPLE 8

(a) 2(R)-N-hydroxy-1-(4-(4-chlorophenoxy)benzenesulfonyl)-4-methyl-piperazine-2-carboxamide hydrochloride To a solution of 313 mg of 2(R)-N-(t-butyldimethylsilyloxy)-4-(t-butoxycarbonyl)-1-(4-(4-chlorophenoxy)benzenesulfonyl)piperazine-2-carboxamide in 2 mL of dichloromethane was added 1 mL of trifluoroacetic acid. After 2 h, 2 mL of methanol was added and the solution was stirred for 15 min and then diluted with 5 mL of toluene. Concentration gave an oily residue, which partitioned between brine/saturated sodium bicarbonate and ethyl acetate. The aqueous layer was extracted with two additional portions of ethyl acetate, and the combined organic layers were dried over sodium sulfate and concentrated to give 231 mg of slightly impure 2(R)-N-hydroxy-1-(4-(4-chlorophenoxy)benzenesulfonyl)-piperazine-2-carboxamide. To a solution of 186 mg of this solid and diisopropylethylamine (0.15 mL) in 3.5 mL of 6:1 acetonitrile:DMF was added iodomethane (0.031 mL). After 1.5 h at 25° C., the reaction was diluted with ca. 5 mL of ethyl acetate and concentrated. The residue was partitioned between 0.5M aqueous sodium bicarbonate and ethyl acetate. The aqueous phase was extracted with a second portion of ethyl acetate, and the combined organic layers were washed with brine, dried over sodium sulfate, and concentrated. The residue was chromatographed on 10 g of silica gel, eluting with gradient of 6% to 8% to 10% methanol in dichloromethane. The product-containing fractions were concentrated, and the residue was dissolved in 5 mL of ethyl acetate:dichloromethane (4:1). To this solution was added 0.4 ML of 1M HCl in ethanol, and the mixture was concentrated to a white residue, which was triturated with ethyl acetate and filtered to give 115 mg of 2(R)-N-hydroxy-1-(4-(4-chlorophenoxy)benzenesulfonyl)-4-methyl-piperazine-2-carboxamide hydrochloride as a white solid: mp 152° C. (decomp).

Anal. calc. for $C_{18}H_{21}Cl_2N_3O_5S$: C, 46.76; H, 4.58; N, 9.09; Cl, 15.34; S, 6.93; Found: C, 46.65; H, 4.65; N, 8.98; Cl, 15.18; S, 6.84.

The following compounds were prepared in a similar manner:

(b) 2(R)-N-hydroxy-1-(4-phenoxybenzenesulfonyl)-4-methylpiperazine-2-carboxamide: mp 127.7° C.;

Anal. calc. for $Cl_8H_{21}N_3O_5S \bullet 0.5$ hexane: C, 56.71; H, 5.98; N, 10.18; Found: C, 56.70; H, 5.99; N, 10.05;

(c) 2(R)-N-hydroxy-1-(4-(4-chlorophenoxy)benzenesulfonyl)-4-(ethoxy-carbonylmethyl)-piperazine-2-carboxamide hydrochloride: mp 163.7° C.;

Anal. calc. for $C_{21}H_{25}Cl_2N_3O_7S$: C, 47.20; H, 4.72; N, 7.86; S, 6.00; Found: C, 47.09; H, 4.77; N, 7.93; S, 5.90; and (d) 2(R)-N-hydroxy-1-(4-(4-fluorophenoxy)benzenesulfonyl)-4-methyl-piperazine-2-carboxamide;

Anal. calc. for $C_{18}H_{20}FN_3O_5S$: C, 52.80; H, 4.92; N, 10.26; S, 7.83; Found: C, 52.66; H, 4.95; N, 10.01; S, 7.56.

The following compound can be prepared in a similar manner:

(e) 2(R)-N-hydroxy-1-(4-(4-fluorophenoxy)benzenesulfonyl)-4-(cyclopropylmethyl)-piperazine-2-carboxamide hydrochloride.

EXAMPLE 9

(a) 2(R)-N-hydroxy-1-(4-(4-chlorophenoxy)benzenesulfonyl)-4-(methanesulfonyl)-piperazine-2-carboxamide To a suspension of 1.00 g of 2(R)-N-(t-butyldimethylsilyloxy)-4(t-butoxycarbonyl)-1-(4-(4-chlorophenoxy)benzenesulfonyl)piperazine-2-carboxamide in 4 mL of dichloromethane was added 3 mL of trifluoroacetic acid, resulting in a clear solution. After 2 h at 25° C., the solution was concentrated to near dryness, and the residue was dissolved in 10 mL of methanol. After 10 min, the solution was reconcentrated, the residual syrup was dissolved in 50 mL of methanol, and ca. 15 mL of IRA-68 weakly basic resin was added. The mixture was stirred gently for 2 h, and then the resin was removed by filtration. The filtrate was concentrated to a white solid, which was triturated with hot t-butyl methyl ether, and after cooling to −20° C., filtered to provide 2(R)-N-hydroxy-1-(4-(4-chlorophenoxy)benzenesulfonyl)-piperazine-2-carboxamide (0.552 g) as a white solid: mp 147.0° C.

To a suspension of 2(R)-N-hydroxy-1-(4-(4-chlorophenoxy)benzenesulfonyl)-piperazine-2-carboxamide (1.03 g) in 20 mL of dichloromethane was added 0.70 mL of triethylamine, 0.41 mL of N-methylmorpholine, and, in a dropwise manner, 0.67 mL of trimethyl-chlorosilane. After 1.5 h, the mixture was cooled to 0° C. and methanesulfonyl chloride (0.20) was added dropwise. The mixture was stirred for 30 min at 0° C. and then allowed to warm to 25° C. After an additional 45 min, the mixture was partitioned between 12.5 mL of 4:1 ethyl acetate:hexane and 50 mL of 0.2M aqueous sodium bisulfate. The organic layer was washed with an additional 50 mL of aqueous sodium bisulfate, and then with 2.5 mL of 1M phosphate buffer (pH 7) and finally with brine. The organic layer was dried over sodium sulfate and concentrated, and the residue was purified by chromatography (75 g of silica gel, eluting with 40% to 50% ethyl acetate:dichloromethane containing 1% acetic acid). First to elute were several mixed fractions, followed by pure product fractions, which were pooled and concentrated. The residue was re-concentrated from toluene (to remove residual acetic acid), and finally from dichloromethane:t-butyl methyl ether to give a white solid. Trituration with 2:1 t-butyl methyl ether:hexane (ca. 15 mL) and filtration gave 2(R)-N-hydroxy-1-(4-(4-chlorophenoxy)benzenesulfonyl)-4-(methanesulfonyl)piperazine-2-carboxamide (0.646 g) as a white powder.

The following compounds were prepared in a similar manner:

(b) 2(R)-N-hydroxy-1-(4-(4-fluorophenoxy)benzenesulfonyl)-4-(methanesulfonyl)-piperazine-2-carboxamide: mp 102.5° C.; and (c) 2(R/S)-N-hydroxy-1-(4-(4-methoxyphenoxy)benzenesulfonyl)-4-(methanesulfonyl)-piperazine-2-carboxamide;

Anal. calc. for $C_{19}H_{32}N_3O_8S_2$: C, 47.00; H, 4.78; N, 8.65; S, 13.21; Found: C, 47.09; H, 4.81; N, 8.57; S, 13.11.

The following compounds can be prepared in a similar manner:

(d) 2(R)-N-hydroxy-1-(4-(pyrid-4-yl)oxybenzenesulfonyl)-4-(methanesulfonyl)-piperazine-2-carboxamide;

(e) 2(R)-N-hydroxy-1-(4-(4-(pyrazol-3-yl)phenoxy)benzenesulfonyl)-4-(methanesulfonyl)-piperazine-2-carboxamide; and (f) 2(R)-N-hydroxy-1-(4-(4-(imidazol-2-yl)phenoxy)benzenesulfonyl)-4-(methanesulfonyl)-piperazine-2-carboxamide.

EXAMPLE 10

(a) 3(R/S)-N-hydroxy-4-(4-bromophenoxybenzenesulfonyl)-tetrahydro-2H-1,4-thiazine-3-carboxamide To a solution of t-butyl-1,2-dibromopropionate (*J. C. S. Perkin I*, p. 1321 (1973); 10.85 g, 37.7 mmol) in chloroform (28 mL) and benzene (20 mL) was added a hot solution of 2-mercaptoethylamine (2.9 g, 37.7 mmol) in chloroform, benzene and triethylamine (11 mL, 79 mmol). This mixture was stirred for 3 days after which it was washed with water and brine. The organic phase was dried (Na₂SO₄), evaporated, and the remaining oil chromatographed on silica (1:1 ethyl acetate/hexane) to give tert-butyl 3(R/S)-tetrahydro-2H-1,4-thiazine-3-carboxylate.

Anal. calc. for $C_9H_{17}NO_2S$: C, 53.17; H, 8.43; N, 6.89; S, 15.77; Found: C, 53.30; H, 8.41; N, 6.96; S, 15.85.

A solution of tert-butyl 1,4-thiomorpholine-3-carboxylate (1.02 g, 5 mmol), 4-(4-bromophenoxy)benzenesulfonyl chloride (1.58 g, 5 mmol), and triethylamine (0.84 mL, 6 mmol) in methylene chloride (10 mL) was stirred at room temperature for 20 hours after which it was diluted with methylene chloride and washed with 3N HCl. The organic phase was dried (Na₂SO₄) and the solvent evaporated. The remaining orange residue was purified by silica gel chromatography (25% ethyl acetate/hexane) to give t-butyl 3(R/S)-4-(4-(4-bromophenoxy)benzenesulfonyl)-tetrahydro-2H-1,4-thiazine-3-carboxylate.

Anal. calc. for $C_{21}H_{24}NO_5S_2Br$: C, 49.03; H, 4.70; N, 2.72; Br, 15.53; Found: C, 48.94; H, 4.67; N, 2.76; Br, 15.62.

A solution of t-butyl 3(R/S)-4-(4-(4-bromophenoxy)benzenesulfonyl)-tetrahydro-2H-1,4-thiazine-3-carboxylate (0.5 g, 0.97 mmol) and trifluoroacetic acid (0.5 mL) in methylene chloride (11 mL) was stirred at room temperature for 1 h, after which it was concentrated to give 3(R/S)-4-(4-(4-bromophenoxy)benzenesulfonyl)tetrahydro-2H-1,4-thiazine-3-carboxylic acid, which was used in the next step without further purification.

To a solution of 3(R/S)-4-(4-(4-bromophenoxy)benzenesulfonyl)tetrahydro-2H-1,4-thiazine-3-carboxylic acid (0.62 g, 1.4 mmol) and O-t-butyldimethylsilyl hydroxylamine (0.27 g, 1.8 mmol) in 6 ml of 5:1 dichloromethane:DMF at 0° C. was added EDC (0.52 g, 2.6 mmol). The mixture was stirred at 0° C. for 30 min and at room temperature for 22 hours and then partitioned between ethyl acetate and water. The organic phase was washed with brine, dried (Na₂SO₄), and concentrated. Purification of the residue by chromatography provided 3(R/S)-N-(t-butyldimethylsilyl)oxy-4-(4-(4-bromophenoxy)benzenesulfonyl)-tetrahydro-2H-1,4-thiazine-3-carboxamide.

A solution of 3(R/S)-N-(t-butyldimethylsilyl)oxy-4-(4-(4-bromophenoxy)benzenesulfonyl)-tetrahydro-2H-1,4-thiazine-3-carboxamide (0.3 g, 0.51 mmol), trifluoroacetic acid (2.5 ml), and methanol (5.5 mL) in methylene chloride (10 mL) was stirred at room temperature for 1 hour. The solvents were evaporated to leave a solid residue which was washed onto filter paper with ether to give 3 (R/S)-N-hydroxy-4-(4-(4-bromophenoxy)benzenesulfonyl)-tetrahydro-2H-1,4-thiazine-3-carboxamide.

Anal. calc. for $C_{17}H_{17}N_2O_5Br$: C, 43.14; H, 3.62; N, 5.92; S, 13.55; Found: C, 43.21; H, 3.66; N, 5.83; S, 13.45.

The following compounds were prepared in a similar manner:

(b) 3(R/S)-N-hydroxy-4-(4-phenoxybenzenesulfonyl)-tetrahydro-2H-1,4-thiazine-3-carboxamide;

Anal. calc. for $C_{17}H_{18}N_2O_5S_2$: C, 51.76; H, 4.60; N, 7.10; S, 16.26; Found: C, 51.81; H, 4.56; N, 7.17; S, 16.18; and (c) 3(R/S)-N-hydroxy-4-(4-(4-fluorophenoxy)benzenesulfonyl)tetrahydro-2H-1,4-thiazine-3-carboxamide;

Anal. calc. for $C_{17}H_{17}N_2O_5Br$: C, 49.50; H, 4.15; N, 6.79; S, 15.55; Found: C, 49.40; H, 4.12; N, 6.72; S, 15.48.

EXAMPLE 11

(a) 1(R/S),3(R/S)-N-hydroxy-1-oxo-4-(4-(4-bromophenoxy)benzenesulfonyl)-tetrahydro-2H-1,4-thiazine-3-carboxamide.

A solution of t-butyl 1(R/S),3(R/S)-4-(4-(4-bromophenoxy)benzenesulfonyl)-tetrahydro-2H-1,4-thiazine-3-carboxylate (0.3 g, 0.38 mmol) and sodium perborate (0.11 g, 0.73 mmol) in acetic acid (3 mL) was stirred at 35° C. for 5 hours, after which it was quenched with saturated aqueous sodium bicarbonate and extracted with ethyl acetate. The organic layer was dried (Na₂SO₄) and concentrated to give a foam which was purified by silica gel chromatography (ethyl acetate) to give t-butyl 1(R/S),3(R/S)-4-(4-(4-bromophenoxy)benzenesulfonyl)-1-oxo-tetrahydro-2H-1,4-thiazine-3-carboxylate: MS (FAB) found 530 (M+H)⁺.

To a solution of t-butyl 1(R/S),3(R/S)-4-(4-(4-bromophenoxy)benzenesulfonyl)-1-oxo-tetrahydro-2H-1,4-thiazine-3-carboxylate (0.18 g, 0.34 mmol) in methylene chloride (4 mL) was added 1.8 mL of trifluoroacetic acid. After 4 h, the solution was concentrated to give 1(R/S),3(R/S)-4-(4-(4-bromophenoxy)benzenesulfonyl)-1-oxo-tetrahydro-2H-1,4-thiazine-3-carboxylic acid, which was used without further purification.

To a solution of 1(R/S),3(R/S)-4-(4-(4-bromophenoxy)benzenesulfonyl)-1-oxo-tetrahydro-2H-1,4-thiazine-3-carboxylic acid (0.08 g, 0.17 mmol) and O-t-butyldimethylsilyl hydroxylamine (0.037 g, 0.25 mmol) in 6:1 dichloromethane:DMF (3.5 mL) at 0° C. was added EDC (0.06 g, 0.34 mmol). The mixture was stirred at 0° C. for 30 minutes followed by room temperature for 3.5 hours and then partitioned between ethyl acetate and water. The organic phase was washed with brine, dried ($Na_2SO_4$) and concentrated. The residue was purified by chromatography (ethyl acetate) to give 1(R/S),3(R/S)-N-(t-butyldimethylsilyl)-oxy-1-oxo-4-(4-(4-bromophenoxy)benzenesulfonyl)tetrahydro-2H-1,4-thiazine-3-carboxamide.

A solution of 1(R/S),3(R/S)-N-(t-butyldimethylsilyl)oxy-1-oxo-4-(4-(4-bromophenoxy)benzenesulfonyl)-tetrahydro-2H-1,4-thiazine-3-carboxamide (0.069 g, 0.11 mmol) and trifluoroacetic acid (0.5 ml) in 2 mL of 1:1 methanol:methylene chloride was stirred at room temperature for 1 hour. The solvents were evaporated to leave a solid residue which was washed onto filter paper with ether and hexane to give 1(R/S),3(R/S)-N-hydroxy-1-oxo-4-(4-(4-bromophenoxy)benzenesulfonyl)-tetrahydro-2H-1,4-thiazine-3-carboxamide.

Anal. calc. for $C_{17}H_{17}N_2O_6S_2Br$: C, 41.72; H, 3.50; N, 5.72; S, 13.10; Br, 16.33; Found: C, 41.81; H, 3.46; N, 5.65; S, 13.01; Br, 16.44.

The following compound was prepared in a similar manner:

(b) 1(R/S),3(R/S)-N-hydroxy-1-oxo-4-(4-(4-fluorophenoxy)benzenesulfonyl)-tetrahydro-2H-1,4-thiazine-3-carboxamide;

Anal. calc. for $C_{17}H_{17}N_2O_6S_2F$: C, 47.66; H, 4.00; N, 6.54; S, 14.97; Found: C, 47.70; H, 4.09; N, 6.45; S, 14.86.

EXAMPLE 12

(a) 6(R)-(N-hydroxycarbamoyl)-1-(4-phenoxy)benzenesulfonyltetrahydropyrimidin-4-one To a solution of D-asparagine (15.0 g) in 400 mL of water at 45° C. was added 8.25 mL of 37% formalin. After 1 h at 45° C., the solution was cooled to −5° C. to give a slurry. The slurry was allowed to warm to 0° C., and the precipitate collected by filtration to give, following drying in vacuo, 2.26 g of 6(R)-carboxy-tetrahydropyrimidin-4-one as a white crystalline solid: $^1$H NMR ($D_2O$, 300 MHz) δ 4.70 and 4.58 (AB quartet, 2H, J=11 Hz), 4.22 (dd, 1H, J=6 and 9 Hz), 3.04 (dd, 1H, J=6 and 16 Hz), 2.82 (dd, 1H, J=9 and 16 Hz).

To a solution of 6(R)-carboxy-tetrahydropyrimidin-4-one in 8 mL of water and 4 mL of dioxane was added 1.5 mL of N-methylmorpholine, followed by a solution of 4-phenoxybenzenesulfonyl chloride (1.88 g) in 4 mL of dioxane. The mixture was stirred for 6 h and then poured into pH 4.0 citrate buffer and extracted with ethyl acetate (2×50 mL). The organic layer was dried over sodium sulfate and concentrated, and the residue chromatographed (15% methanol in dichloromethane containing 1% acetic acid) to give 4R-carboxy-1-(4-phenoxy)benzenesulfonyl-tetrahydropyriimidin-4-one as a white solid: $^1$H NMR ($D_2O$, 300 MHz) δ 7.86 (d, 2H, J=9 Hz), 7.48 (t, 2H, J=8 Hz), 7.29 (t, 1H, J=7 Hz), 7.11–7.18 (m, 4H), 5.03 (d, 1H, J=14 Hz), 4.68 (d, 1H, J=14 Hz), 4.31 (t, 1H, J=7 Hz), 2.68 (dd, 1H, J=17 and 7 Hz), 2.47 (dd, 1H, J=17 and 8 Hz).

To a solution of 215 mg of 6(R)-carboxy-1-(4-phenoxy)benzenesulfonyl-tetrahydropyrimidin-4-one in 5.5 mL of 10:1 dichloromethane:DMF was added O-(t-butyldimethylsilyl)hydroxylamine (126 mg) followed by EDC hydrochloride (131 mg). After 4 h, the reaction was partitioned between 1:1 ethyl acetate:hexane and aqueous sodium bicarbonate. The organic layer was dried over sodium sulfate, concentrated, and the residue was rapidly chromatographed with 20% ethyl acetate in dichloromethane to give 6(R)-(N-(t-butyldimethylsilyl)oxycarbamoyl)-1-(4-phenoxy)benzene sulfonyl-tetrahydropyrimidin-4-one as a solid, which, without further purification, was dissolved in 5 mL of methanol and 0.2 mL of trifluoroacetic acid. After 1 h, 5 mL of toluene was added and the solution was concentrated. The residue was purified by rotary chromatography (65:20:15 dichloromethane:ethyl acetate:ethanol containing 0.5% acetic acid) to give 6(R)-(N-hydroxycarbamoyl)-1-(4-phenoxy)benzenesulfonyl-tetrahydropyrimidin-4-one (31 mg) as a white solid: $^1$H NMR (methanol-$d_4$, 300 MHz) δ7.90 (d, 2H, J=9 Hz), 7.47 (t, 2H, J=8.7 Hz), 7.27 (t, 1H, J=7 Hz), 7.09–7.16 (m, 4H), 5.02 (d, 1H, J=14 Hz), 4.80 (d, 1H, J=14 Hz), 4.37 (t, 1H, J=7 Hz), 2.77 (dd, 1H, J=17 and 7 Hz), 2.72 (dd, 1H, J=17 and 8 Hz).

The following compounds were prepared in a similar manner:

(b) 6(R)-(N-hydroxycarbamoyl)-1-(4-(4-fluorophenoxy)benzenesulfonyl)-tetrahydropyrimidin-4-one;

Anal. calc. for $C_{17}H_{16}FN_3O_6S$: C, 49.87; H, 3.94; N, 10.26; S, 7.83; Found: C, 49.84; H, 3.95; N, 10.18; S, 7.73;

(c) 6(R)-(N-hydroxycarbamoyl)-1-(4-(4-chlorophenoxy)benzenesulfonyl)-tetrahydropyrimidin-4-one;

(d) 6(R)-(N-hydroxycarbamoyl)-1-(4-(4-methoxyphenoxy)benzenesulfonyl)-tetrahydropyrimidin-4-one; and (e) 6(R)-(N-hydroxycarbamoyl)-1-(4-(4-(fur-2-yl)phenoxy)benzenesulfonyl)-tetrahydropyrimidin-4-one.

EXAMPLE 13

(a) 3(S)-N-hydroxy-4-(4-(4-bromophenoxy)benzenesulfonyl)-2,2-dimethyl-tetrahydro-2H-1,4-thiazine-3-carboxamide A suspension of D-penicillamine (0.5 g, 3.35 mmol) in methanol was cooled to 0° C. and powdered sodium hydroxide (0.28 g, 7.04 mmol) was added in one portion to give a colorless solution. 2-Bromoethanol (0.24 mL, 3.35 mmol) was added and the reaction mixture stirred at 0° C. for 25 minutes and room temperature for an additional 80 min. The solvent was evaporated and the solid residue was treated with water, brought to pH 3 with 6N HCl and reconcentrated. The resulting oily residue was dissolved in water (6 mL) and stirred with DMF, sodium carbonate (1.17 g, 11.04 mmol) and 4-(4-bromophenoxy)benzenesulfonyl chloride (1.28 g, 3.68 mmol) for 17 h. The solution was diluted with water and washed with ethyl acetate. The aqueous layer was acidified to pH 1.5 with concentrated HCl and extracted with ethyl acetate. The organic extracts were combined, washed with water and brine and dried. The solution was filtered, evaporated and azeotroped from benzene to give the crude acid as a viscous oil (0.807 g; 48% yield).

A portion of this oil was dissolved in DMA (3 mL), treated with potassium carbonate (2.4 g, 17.5 mmol), benzyltriethylammonium chloride (0.15 g, 0.67 mmol) and t-butyl bromide (3.7 mL, 32 mmol). The reaction mixture was stirred vigorously for 18.5 h at 55° C., after which it was diluted with ethyl acetate, washed with water, dried and evaporated to give a viscous oil which was purified by silica gel chromatography (50% ethyl acetate:hexane) to give 2(S)-3-( 2-hydroxyethylsulfanyl )-3-methyl-2- (4-(4-bromophenoxy)benzenesulfonylamino)-butyric acid tert-butyl ester as a colorless, viscous glass.

Anal. calc. for $C_{23}H_{30}NO_6S_2Br$: C, 49.28; H, 5.39; N, 2.50; S, 11.44; Br, 14.25; Found: C, 49.21; H, 5.25; N, 2.46; S, 11.37; Br, 14.31.

To a solution of 2(S)-3-(2-hydroxyethylsulfanyl)-3-methyl-2-(4-(4-bromophenoxy)benzenesulfonylamino)-butyric acid tert-butyl ester (0.17 g, 0.30 mmol) in THF (5 mL) was added triphenylphosphine (0.102 g, 0.39 mmol) and diethylazodicarboxylate (0.61 mL, 0.39 mmol). After stirring at room temperature for 20 min, the solvent was evaporated and the product purified on silica gjel (40% ethyl acetate:hexane) to give tert-butyl 3(S)-4-(4-(4-bromophenoxy)-benzenesulfonyl)-2,2-dimethyl-tetrahydro-2H-1,4-thiazine-3-carboxylate as a light yellow oil.

Anal. calc. for $C_{23}H_{28}NO_5S_2Br$: C, 50.92; H, 5.20; N, 2.50; S, 11.82; Found: C, 51.03; H, 5.18; N, 2.95; S, 11.33.

A solution of tert-butyl 3(S)-4-(4-(4-bromophenoxy)benzenesulfonyl)-2,2-dimethyltetrahydro-2H-1,4-thiazine-3-carboxylate (0.12 g, 0.22 mmol) in dichloromethane (2 mL) and TFA (1 mL) was stirred at room temperature for 50 min, after which the solvents were evaporated and the residue azeotroped from benzene to give 3(S)-4-(4-(4-bromophenoxy)benzenesulfonyl)-2,2-dimethyltetrahydro-2H-1,4-thiazine-3-carboxylic acid as a white solid, which was next used without further purification.

A solution of 3(S)-4-(4-(4-bromophenoxy)benzenesulfonyl)-2,2-dimethyl-tetrahydro-2H-1,4-thiazine-3-carboxylic acid (0.11 g, 0.22 mmol), O-t-butyldimethlsilyl hydroxylamine (0.049 g, 0.33 mmol) and EDC (0.085 g, 0.44 mmol) in dichloromethane (2 mL) was stirred at room temperature for 30 min, after which the reaction mixture was diluted with dichloromethane (30 mL), washed with 5% citric acid and saturated sodium bicarbonate, dried and evaporated to give crude 3(S)-N-(t-butyldimethylsilyl)oxy-4-(4-(4-bromophenoxy)benzenesulfonyl)-2,2-dimethyl-tetrahydro-2H-1,4-thiazine-3-carboxamide, which was next used without further purification.

A solution of 3(S)-N-(t-butyldimethylsilyl)oxy-4-(4-(4-bromophenoxy)benzenesulfonyl)-2,2-dimethyl-tetrahydro-2H-1,4-thiazine-3-carboxamide (0.12 g, 0.19 mmol) and trifluoroacetic acid (2 mL) in dichloromethane (2 mL) was stirred at room temperature for 1 h, after which the solvents were evaporated and the residue was azeotroped from benzene. The product was triturated with diethyl other, filtered and washed with diethyl ether to give 3(S)-N-hydroxy-4-(4-(4-bromophenoxy) benzenesulfonyl)-2,2-dimethyl-tetrahydro-2H-1,4-thiazine-3-carboxamide.

Anal. calc. for $C_{19}H_{21}N_2O_5S_2Br$: C, 45.51; H, 4.22; N, 5.59; S, 12.79; Br, 15.94; Found: C, 45.31; H, 4.17; N, 5.50; S, 12.69; Br, 16.09.

The following compounds can be prepared from 1) pencillamine in a similar manner:

(b) 3(S)-N-hydroxy-2,2-dimethyl-4-(4-(4-fluorophenoxy) benzenesulfonyl)-tetrahydro-2H-1,4-thiazine-3-carboxamide; and (c) 3(S)-N-hydroxy-2,2-dimethyl-4-(4-(4-(imidaz-2-yl) phenoxy)benzene-sulfonyl)-tetrahydro-2H-1,4-thiazine-3-carboxamide.

EXAMPLE 14

(a) 1(R),3(S)-N-hydroxy-4-(4-(4-bromophenoxy) benzenesulfonyl)-2,2-dimethyl-1-oxo-tetrahydro-2H-1,4-thiazine-3-carboxamide A solution of t-butyl 3(S)-4-(4-(4-bromophenoxy) benzenesulfonyl)-2,2-dimethyltetrahydro-2H-1,4-thiazine-3-carboxylate (0.65 g, 1.2 mmol) in acetic acid (2 mL) was treated with NaBO3•4H2O (0.23 g, 1.5 mmol) and stirred at room temperature for 2 h, after which the reaction mixture was diluted with ethylactate, washed with water and saturated sodium bicarbonate, dried over sodium sulfate and evaporated. The foamy residue was twice chromatographed on silica gel (20% hexane:ethyl acetate) to give t-butyl 1(R),3(S)-4-(4-(4-bromophenoxy)benzenesulfonyl)-2,2-dimethyl-1-oxo-tetrahydro2H-1,4-thiazine-3-carboxylate as a white foam.

Anal. calc. for $C_{23}H_{28}NO_6S_2Br$: C, 49.46; H, 5.05; N, 2.51; S, 11.48; Br, 14.31; Found: C, 49.44; H, 5.11; N, 2.53; S, 11.55; Br, 14.21.

A solution of t-butyl 1(R),3(S)-4-(4-(4-bromophenoxy) benzenesulfonyl)-2,2-dimethyl-1-oxo-tetrahydro-2H-1,4-thiazine-3-carboxylate (0.37 g, 0.66 mmol) in dichloromethane (4 mL) and TFA (4 mL) was stirred at room temperature for 7 h, after which the solvents were evaporated and the residue azeotroped from benzene. The product was triturated with a warm 50% diethyl ether:hexane solution and filtered to give 1(R),3(S)-4-(4-(4-bromophenoxy) benzenesulfonyl)-2,2-dimethyl-1-oxo-tetrahydro-2H-1,4-thiazine-3-carboxylic acid as a white solid.

Anal. calc. for $C_{19}H_{20}NO_6S_2Br$: C, 45.42; H, 4.01; N, 2.79; S, 12.76; Br, 15.90; Found: C, 45.51; H, 4.08; N, 2.84; S, 12.66; Br, 15.83.

A solution of 1(R),3(S)-4-(4-(4-bromophenoxy) benzenesulfonyl)-2,2-dimethyl-1-oxo-tetrahydro-2H-1,4-thiazine-3-carboxylic acid (0.32 g, 0.64 mmol) in dichloromethane (3 mL) and DMF (1 mL) was cooled to 0° C. and treated with O-t-butyldimethylsilyl hydroxylamine (0.11 g, 0.76 mmol) immediately followed by EDC (0.183 g, 0.96 mmol). The resulting reaction mixture was stirred at 0° C. for 80 min, after which additional O-t-butyldimethylsilyl hydroxylamine (0.094 g, 0.64 mmol) and EDC (0.15 g, 0.76 mmol) were added, and the mixture was stirred at 0° C. for an additional hour and at room temperature for 1 h. The reaction mixture was diluted with ethyl acetate and washed with 5% citric acid, water and saturated sodium bicarbonate, to give 1(R),3(S)-N-(t-butyldimethylsilyl)oxy-4-(4-(4-bromophenoxy)benzenesulfonyl)-2,2-dimethyl-1-oxo-tetrahydro-2H-1,4-thiazine-3-carboxamide, which was next used without further purification.

A solution of 1(R),3(S)-N-(t-butyldimethylsilyl)oxy-4-(4-(4-bromophenoxy)benzenesulfonyl)-2,2-dimethyl-1-oxo-tetrahydro-2H-1,4-thiazine-3-carboxylic acid O-t-butyldimethylsilyl hydroxamide (0.13 g, 0.21 mmol) in dichloromethane (2 mL) and TFA (1 mL) was stirred at room temperature for 2 h, after which the solvents were evaporated and the residue was azeotroped from benzene. The resulting white solid was filtered and washed with diethyl ether to give 1(R),3(S)-N-hydroxy-4-(4-(4-bromophenoxy)-benzenesulfonyl)-2,2-dimethyl-1-oxo-tetrahydro-2H-1,4-thiazine-3-carboxamide.

Anal. calc. for $C_{19}H_{21}N_2O_6S_2Br$: C, 44.10; H, 4.09; N, 5.41; S, 12.39; Found: C, 43.84; H, 4.20; N, 5.37; S, 12.25.

The following compound can be prepared in a similar manner:

(b) 1(R),3(S)-N-hydroxy-1-oxo-2,2-dimethyl-4-(4-(4-fluorophenoxy)benzenesulfonyl)-tetrahydro-2H-1,4-thiazine-3-carboxamide.

EXAMPLE 15

(a) 3(S)-N-hydroxy-4-(4-((pyrid-4-yl)oxy) benzenesulfonyl)-2,2-dimethyl-tetrahydro-2H-1,4-thiazine-3-carboxamide To a stirred solution of D-penicillamine in 20 mL of dry DMF as added diisopropylethylamine (1.74 mL) followed by, in a dropwise manner, trimethylsilyl chloride (1.52 mL). After 30 min, diazabicyclo[4.2.0]undecane (4.48 mL) was added to the clear solution, and the resulting solution was slowly transferred via cannula over a 1 h period to a solution of 1,2-dibromoethane (0.95 mL) in 20 mL of dry DMF at 50° C. After the addition was complete, the solution was heated for an additional 1 h at 50° C., and then cooled to 0° C. To the stirred solution was added N-methylmorpholine (1.00 mL), followed by 9-fluorenylmethoxycarbonyl chloride (2.84 g), and the solution was kept at −20° C. for 16 h. An additional 0.50 g of 9-fluorenylmethoxycarbonyl chloride was added, and the solution was stirred for an additional 1 h at 0° C. and then quenched with 1 mL of water. The reaction was partitioned between 3:1 ethyl acetate:hexane (200 mL) and 0.2N aqueous sodium bisulfate (200 mL). The organic layer was washed with additional 0.2N aqueous sodium bisulfate solution (150 mL) and with brine (50 mL), dried over sodium sulfate and concentrated. The residue was purified by chromatography on 150 g of silica gel, eluting with 25% to 35% ethyl acetate:hexane containing 0.5% acetic acid. The product-containing fractions were concentrated to give a syrup, which was twice concentrated from toluene, and finally from t-butyl methyl ether:isooctane, to give 2.84 g of 3(S)-4-(9-fluorenylmethoxy-carbonyl)-2,2-dimethyl-tetrahydro-2H-1,4-thiazine-3-carboxylic acid as a white solid.

To a solution of 3(S)-4-(9-fluorenylmethoxycarbonyl)-2,2-dimethyl-tetrahydro-2H-1,4-thiazine-3-carboxylic acid (2.98 g) in 20 mL of dichloromethane at 0° C. was added O-(t-butyldiphenylsilyl) hydroxylamine (2.71 g) followed by EDC hydrochloride (1.58 g). The reaction was stirred at 0° C. to 25° C. for 16 h and then partitioned between 1:1 ethyl acetate:hexane (200 mL) and 0.2N pH 7 phosphate buffer (100 mL). The organic layer was washed with brine, dried over sodium sulfate and concetrated. The residue was purified by chromatography on 150 g of silica gel, eluting with 20% to 30% ethyl acetate:hexane, to provide, after concentration from dichloromethane:isooctane, 3(S)-N-(t-butyldiphenylsilyl)oxy-4-(9-fluorenylmethoxycarbonyl)-2,2-dimethyl-tetrahydro-2H-1,4-thiazine-3-carboxamide (4.42 g) as a white solid.

To a solution of 3(S)-N-(t-butyldiphenylsilyl)oxy-4-(9-fluorenylmethoxycarbonyl)-2,2-dimethyl-tetrahydro-2H-1,4-thiazine-3-carboxamide (4.33 g) in THF (10 mL) was added diethylamine (5 mL). After 1 h, the solution was concentrated and the residue was chromatographed on 75 g of silica gel, eluting with ethyl acetate, to give 3(S)-N-(t-butyldiphenylsilyl)oxy-2,2-dimethyl-tetrahydro-2H-1,4-thiazine-3-carboxamide (2.11 g) as a sticky solid foam.

To a solution of 4-phenoxypyridine (6.84 g) in 20 mL of 1,2-dichloroethane at 0° C. was added 8.0 mL of chlorosulfonic acid in a dropwise manner. After 10 min, the ice bath was removed and the solution was allowed to warm to 25° C. After an additional 1 h, the solution was heated to 40° C. for 3 h, and then cooled to 25° C., and oxalyl chloride (4.4 mL) was added. The solution was heated to 50° C. for 16 h, and then an additional 2.2 mL of oxalyl chloride was added. After 5 h more at 50° C., the solution was cooled to 25° C., and poured with rapid stirring into 250 mL of diethyl ether. After 1 min, the solids were allowed to settle and the supernatant was decanted. The residue was suspended in 3:1 toluene:dichloromethane (250 mL) at about 5° C. and 50 mL of 1.6M aqueous $K_3PO_4$ was added with stirring. After about 30 seconds, the mixture was transferred to a separatory funnel and the layers were separated. The organic layer was washed with 25 mL of 1N pH 7 phosphate buffer and with 10 mL of brine, and the combined aqueous layers were extraceted with 50 mL of toluene. The combined organic layers were dried over sodium sulfate then filtered through a glass-fiber filter. To the filtrate was immediately added 11 mL of 4M HCl in dioxane and the solution was then concentrated. Partial concentration from dichloromethane:t-butyl methyl ether and filtration gave 2.11 g of 4-((pyrid-4-yl)oxy)benzenesulfonyl chloride hydrochloride.

To a solution of 3(S)-N-(t-butyldiphenylsilyl)oxy-2,2-dimethyl-tetrahydro-2H-1,4-thiazine-3-carboxamide (2.11 g) in dichloromethane (20 mL) at 0° C. was added N-methylmorpholine (1.35 mL) followed by 4-((pyrid-4-yl)oxy)benzenesulfonyl chloride hydrochloride (1.71 g). The solution was stirred at 0° C. for 3 h, and then at 25° C. for 4 h. The reaction was partitioned between 3:1 ethyl acetate:hexane (150 mL) and 0.5N pH 7 phosphate buffer (50 mL). The organic layer was washed with additional buffer and with brine, dried over sodium sulfate and concentrated. The residue was chromatographed on 150 g of silica gel, eluting with 30% to 50% ethyl acetate:dichloromethane to give, after partial concentration from dichloromethane:isooctane, 3(S)-N-(t-butyldiphenylsilyl)oxy-4-(4-((pyrid-4-yl)oxy)benzenesulfonyl)-2,2-dimethyl-tetrahydro-2H-1,4-thiazine-3-carboxamide (2.36 g) as a pale yellow solid.

To a solution of 3(S)-N-(t-butyldiphenylsilyl)oxy-4-(4-((pyrid-4-yl) oxy)benzenesulfonyl)-2,2-dimethyl-tetrahydro-2H-1,4-thiazine-3-carboxamide (2.25 g) in methanol (10 mL) was added 5 mL of a 10% solution of concentrated HCl in methanol. After 1 h at 25° C., the solution was diluted with methanol (50 mL) and treated with Amberlite IRA-68 weakly basic resin (about 15 mL) until the pH measured 7.2. The resin was removed by filtration and washed well with methanol, and then the filtrate was concentrated to about 10 mL. Addition of 20 mL of t-butyl methyl ether gave a voluminous precipitate, which was collected by filtration to give 1.19 g of an off-white solid. The solid was dissolved in 50 mL of 10% methanol in ethyl acetate and filtered through a 0.45 μm syringe filter to remove trace particles. The filtrate was partially concetrated to about 20 mL, diluted with additional ethyl acetate and reconcentrated to about 20 mL. The crystalline precipitate was collected by filtration and dried in vacuo to give 3(S)-N-hydroxy-4-(4-((pyrid-4-yl)oxy)benzenesulfonyl)-2,2-dimethyl-tetrahydro-2H-1,4-thiazine-3-carboxamide (0.97 g) as a white solid: mp 149.8° C.

Anal. calc. for $C_{18}H_{21}N_3O_5S_2 \bullet 0.5\ H_2O$: C, 49.47; H, 5.19; N, 9.62; S, 14.67; Found: C, 49.49; H, 5.15; N, 9.37; S, 14.41.

The following compound was prepared in a similar manner:

(b) 3(S)-N-hydroxy-4-(4-((pyrid-2-yl)oxy) benzenesulfonyl)-2,2-dimethyl-tetrahydro-2H-1,4-thiazine-3-carboxamide;

Anal. calc. for $C_{18}H_{21}N_3O_5S_2 \bullet 0.75\ H_2O$: C, 49.47; H, 5.19; N, 9.62; S, 14.67; Found: C, 49.22; H, 4.81; N, 9.57; S, 14.69;

High Resolution MS (FAB) calc.: 556.9977; found: 556.9963.

The following compounds can be prepared in a similar manner:

(c) 3(S)-N-hydroxy-4-(4-((imidazol-2-yl)phenoxy)benzenesulfonyl)-2,2-dimethyl-tetrahydro-2H-1,4-thiazine-3-carboxamide; and (d) 3(S)-N-hydroxy-4-(4-((imidazol-1-yl)phenoxy)benzenesulfonyl)-2,2-dimethyl-tetrahydro-2H-1,4-thiazine-3-carboxamide.

The results obtained during biological testing of some preferred embodiments of the inventive compounds are described below.

Biological Data

Enzyme Assays

Stromelysin enzymatic activity was measured using a modified version of a resonance energy transfer fluorogenic assay as described in FEBS, vol. 296(3), p. 263 (1992). The MCA-peptide substrate is shown below. The fluorescent MCA group is quenched by resonance energy transfer to the 2,4-dinitrophenyl group. Matrix metalloproteinases cleave this substrate at the Gly-Leu bond. Cleavage results in the loss of energy transfer and a large increase in fluorescence of the MCA group.

Fluorescence data was collected with Perkin-Elmer LS-5B and LS-5B spectrofluorimeters with $\lambda_{excitation}$=328 nm and $\lambda_{emission}$=393 nm. Spectrofluorimeters were interfaced with IBM-compatible microcomputer systems.

Competitive Inhibition Analyses

The $K_m$ for the MCA peptide substrate with the matrix metalloproteinases is quite high and exceeds its solubility under assay conditions. Consequently, the apparent $K_i$ ($K_{i,app}$) was determined to describe the strength of inhibition. However, in this case, $K_{i,app}$ would be essentially equal to $K_i$ since $[S]<<K_m$. For the determination of $K_{i,app}$, the concentration of the inhibitor was varied at a constant and low concentration of substrate and the steady-state rates of fluorescence change determined. In most cases absorptive quench due to the presence of ligand was not observed. For slow-binding inhibitors, onset of inhibition curves were collected for at least 45 minutes so that equilibrium was established. Steady-state rates of fluorescence change were obtained by fitting a curve to an equation for a single exponential decay containing a linear phase. The fitted value of the linear phase was taken as the steady-state rate. The steady-state rates were fitted to the Michaelis equation describing competitive inhibition by non-linear methods.

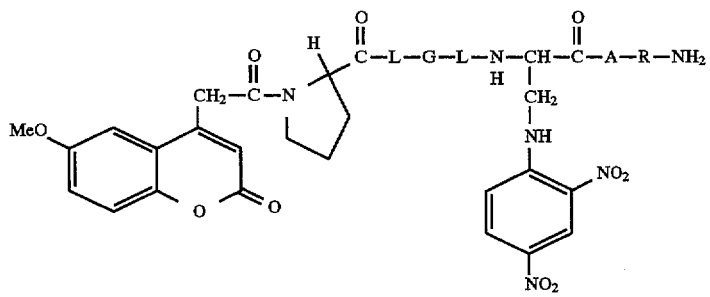

7-methoxycoumarin-4-yl-acetyl-pro-leu-gly-leu-3-(2,4-dinitrophenyl)-L-2,3-diaminoproprionyl-ala-arg-NH$_2$ The MCA assay was performed at 37° C. in buffer containing 50 mM Tricine (pH 7.5), 10 mM CaCl$_2$, 200 mM NaCl, and 1% DMSO with the following concentrations of matrix metalloproteinases: 1.4 nM stromelyin, 0.063 nM matrilysin, and 0.030 µM gelatinase A. The concentration of MCA substrate was 10 or 20 µM in a final volume of 1.6 mL.

Data resulting from tight-binding inhibition was analyzed, and $K_{i,app}$ determined by fitting the data to the tight-binding equation of Morrison (Biochem. Biophys. Acta, vol. 185, pp. 269–286 (1969)) by non-linear methods.

The results of the above-described tests are presented below in Table 1.

TABLE 1

Enzyme Inhibition Constants ($K_i$) nM

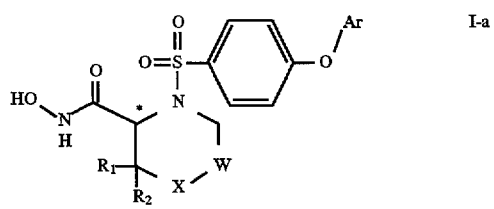

I-a

| | Variable | | | | Enzyme | | | | |
|---|---|---|---|---|---|---|---|---|---|
| * | W | X | Ar | R$_1$/R$_2$ | HSLN | Matr. | HFC | HG72kD | Coll3 |
| R/S | CH$_2$ | N−CO$_2$C(CH$_3$)$_3$ | 4-bromophenyl | H/H | 0.730 | 378.00 | 60.00 | 0.025 | 0.070 |
| R/S | CH$_2$ | N−H (HCl salt) | 4-bromophenyl | H/H | 1.800 | 263.00 | 68.00 | 0.770 | 1.100 |
| R/S | CH$_2$ | N−COCH$_3$ | phenyl | H/H | 0.640 | 113.00 | — | 0.110 | 0.050 |
| R/S | CH$_2$ | N−CH$_3$ | 4-bromophenyl | H/H | 1.400 | 1860.00 | 257.00 | 0.035 | 0.022 |
| R/S | CH$_2$ | N−CONHCH$_3$ | 4-chlorophenyl | H/H | 0.406 | 109.00 | — | 0.034 | 0.016 |

TABLE 1-continued

Enzyme Inhibition Constants (K$_i$) nM

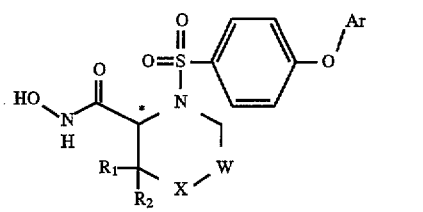

I-a

| | | Variable | | | | | Enzyme | | |
|---|---|---|---|---|---|---|---|---|---|
| * | W | X | Ar | R$_1$/R$_2$ | HSLN | Matr. | HFC | HG72kD | Coll3 |
| R/S | CH$_2$ | S | 4-bromophenyl | H/H | 0.333 | 169.00 | — | 0.040 | — |
| R/S | CH$_2$ | N—H | phenyl | H/H | 6.200 | 560.00 | — | 0.864 | — |
| R/S | CH$_2$ | S | phenyl | H/H | 0.647 | 201.00 | — | 0.025 | 0.029 |
| R/S | CH$_2$ | N—SO$_2$CH$_3$ | 4-chlorophenyl | H/H | 0.150 | 44.00 | 5.50 | 0.022 | 0.015 |
| R/S | CH$_2$ | N—CH$_3$ | phenyl | H/H | 6.300 | 2177.00 | — | 0.101 | 0.158 |
| R | CH$_2$ | O | 4-chlorophenyl | H/H | 0.093 | 77.00 | 8.90 | 0.031 | 0.021 |
| R | CH$_2$ | N—CH$_3$ (HCl salt) | 4-chlorophenyl | H/H | 0.670 | 993.00 | 130.00 | 0.025 | 0.020 |
| R | CH$_2$ | N—H (HCl salt) | 4-chlorophenyl | H/H | 1.000 | 171.00 | 34.00 | 0.413 | 0.363 |
| R | CH$_2$ | N—SO$_2$CH$_3$ | 4-chlorophenyl | H/H | 0.043 | 28.00 | 2.50 | 0.003 | 0.002 |
| R/S | CH$_2$ | S=O | 4-bromophenyl | H/H | 0.410 | 109.00 | 23.00 | 0.013 | 0.017 |
| R/S | CH$_2$ | N—CO$_2$C(CH$_3$)$_3$ | 4-cyanophenyl | H/H | 14.000 | 3570.00 | 580.00 | 0.696 | 1.97 |
| R/S | CH$_2$ | N—CO$_2$C(CH$_3$)$_3$ | 2-pyridyl | H/H | 17.000 | 2850.00 | 550.00 | 0.716 | 1.00 |
| R/S | CH$_2$ | S | 4-fluorophenyl | H/H | 0.530 | 313.00 | 40.00 | 0.028 | 0.035 |
| R/S | CH$_2$ | S=O | 4-fluorophenyl | H/H | 0.790 | 306.00 | 28.00 | 0.034 | 0.016 |
| R | CH$_2$ | N—CO$_2$C(CH$_3$)$_3$ | 4-fluorophenyl | H/H | 0.490 | 220.00 | 18.00 | 0.026 | — |
| R | CH$_2$ | N—H (HCl salt) | 4-fluorophenyl | H/H | 0.980 | 365.00 | 44.00 | 0.232 | 0.257 |
| R | CH$_2$ | N—SO$_2$CH$_3$ | 4-fluorophenyl | H/H | 0.130 | 52.00 | 4.70 | 0.007 | 0.005 |
| S | N—H | C=O | phenyl | H/H | 4.600 | 1300.00 | 210.00 | 0.057 | 0.124 |
| S | CH$_2$ | S | 4-bromophenyl | CH$_3$/CH$_3$ | 0.017 | 2.80 | 0.56 | 0.003 | 0.001 |
| R | CH$_2$ | S=O | 4-bromophenyl | CH$_3$/CH$_3$ | 0.056 | — | — | 0.009 | 0.010 |
| R | CH$_2$ | N—CH$_2$CO$_2$CH$_2$CH$_3$ (HCl salt) | 4-chlorophenyl | H/H | 0.250 | 240.00 | 48.00 | — | — |
| R | CH$_2$ | N—SO$_2$CH$_3$ | 4-methoxyphenyl | H/H | 0.190 | 74.00 | 16.00 | — | — |
| R | N—H | C=O | 4-fluorophenyl | H/H | 5.100 | 1840.00 | 187.00 | 0.152 | — |
| S | CH$_2$ | S | 4-pyridyl | CH$_3$/CH$_3$ | 0.170 | 54.00 | 8.20 | 0.083 | 0.038 |
| R | CH$_2$ | N—H | 4-fluorophenyl | H/H | 1.900 | 2060.00 | 176.00 | 0.410 | 0.013 |
| S | CH$_2$ | S | 2-pyridyl | CH$_3$/CH$_3$ | 0.450 | — | — | — | — |
| R | CH$_2$ | N—CO$_2$C(CH$_3$)$_3$ | 4-chlorophenyl | H/H | 0.310 | 142.00 | — | 0.007 | 0.006 |

Tumor models

Primary subcutaneous tumors were established in female BDF, mice by trocar innoculation of the murine Lewis lung carcinoma (NIH) tumor line. This tumor line produces spontaneous lung metastases which arise from the primary tumor. Primary tumor growth was monitored by measuring the length and width of the subcutaneous tumor using calipers; lung metastases were counted at the end of the experiment (22 days after tumor implantation) by removing the lungs and counting the lesions using a dissecting microscope. The test compound was administered daily, i.p., beginning 24 hours after tumor implantation (day 1) and continuing through day 21. Primary tumor volumes and number of lung metastases were compared to control animals using an ANOVA followed by a comparison of means using the F statistic. For example, the compound of example 9(a), at a dosage of 50 mg/kg, produced a statistically significant (p<0.025) tumor growth delay, calculated as the delay in reaching 1000 mm$^3$ tumor volume between control and treated animals, and in the number of lung metastases (p<0.05) relative to the control. All drugs were administered at 50 mg/kg, i.p., daily, Day 1-Day 21. The results are presented in Table 2.

TABLE 2

| Example No. | Tumor Growth Delay | % Inhibition of Lung Metastases |
|---|---|---|
| 5(a) | 2.0 days | 13.6% |
| 8(a) | −0.1 days | 7.5% |
| 7(a) | 0.0 days | 16.1% |
| 9(a) | 7.2 days (p < 0.025) | 77.6% (p < 0.05) |

Arthritis model

Previously frozen bovine nasal cartilage plugs weighing approximately 20 mg were embedded in polyvinyl sponges impregnated with Myobacterium tuberculosis and implanted subcutaneously in female Lewis rats. Dosing was begun 9 days after implantation and the plugs were harvested about one week later. The plugs were weighed and then hydrolyzed and the hydroxyproline content measured. Efficaciousness was determined by the comparison of the compound-treated groups with vehicle-treated controls. The results are presented in Table 3.

TABLE 3

| Example No. | dose p.o. (mg/kg/day) | weight loss % inhibition | hydroxyproline % protection |
|---|---|---|---|
| 3(a) | 25 | 97.5 | n.d. |
| 2(b) | 25 | 81.1 | n.d. |
| 5(a) | 10 | 59.6 | 72.5 |
| 7(a) | 10 | 77.4 | 86.7 |

$p < 0.01$ for all entries;
n.d. = not determined

We claim:

1. A compound of the formula I

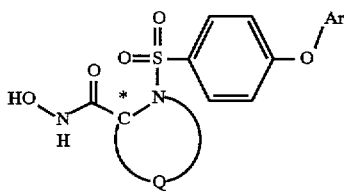

wherein:

Q is a divalent radical having four ring atoms which together with C* and N form a six-membered ring, where each of said four ring atoms independently is unsubstituted or substituted by a suitable substituent, and at least one of said four ring atoms is a heteroatom selected from O, N and S, and the remainder are carbon atoms; and Ar is an aryl or heteroaryl group;

or a pharmaceutically acceptable prodrug or a pharmaceutically acceptable salt thereof.

2. A compound as claimed in claim 1 having the formula I-a

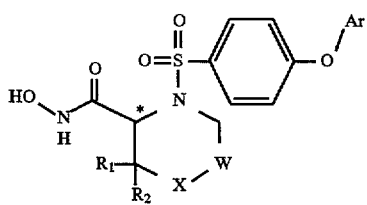

wherein:

W and X are each, independently of one another, $CH_2$, C=O, S, S=O, O, N—$R_3$, or $N^+(O^-)$-$R_4$, where $R_3$ is a hydrogen atom or a suitable substituent, and $R_4$ is a lower alkyl group, provided that when one of W and X is $CH_2$ or C=O, the other is not $CH_2$ or C=O;

$R_1$ and $R_2$ are each, independently of one another, a hydrogen atom, a lower alkyl group, a hydroxycarbonyl group, an alkoxycarbonyl group, an alkylaminocarbonyl group or a dialkylaminocarbonyl group, or $R_1$ and $R_2$ together form a cycloalkyl or heterocycloalkyl ring; and Ar is an aryl or heteroaryl group;

or a pharmaceutically acceptable prodrug thereof or a pharmaceutically acceptable salt thereof.

3. A compound as claimed in claim 2 wherein W is $CH_2$ and X is S, S=O, O, N—$R_3$ or $N^+(O^-)$-$R_4$; or a pharmaceutically acceptable prodrug thereof or a pharmaceutically acceptable salt thereof.

4. A compound as claimed in claim 3 wherein $R_3$ is a hydrogen atom, an alkyl group, an alkylcarbonyl, an alkoxy- carbonyl group, an alkylaminocarboyl group, a dialkylaminocarbonyl, an alkylsulfonyl group or an arylsulfonyl group; or a pharmaceutically acceptable prodrug or a pharmaceutically acceptable salt thereof.

5. A compound as claimed in claim 2 wherein W is S, O or N—$R_3$ and X is $CH_2$; or a pharmaceutically acceptable prodrug or a pharmaceutically acceptable salt thereof.

6. A compound as claimed in claim 2 wherein W is N—$R_3$ and X is C=O; or a pharmaceutically acceptable prodrug or a pharmaceutically acceptable salt thereof.

7. A compound as claimed in claim 2 wherein W is C=O and X is S, O or N—$R_3$; or a pharmaceutically acceptable prodrug or a pharmaceutically acceptable salt thereof.

8. A compound as claimed in claim 2 wherein Ar is an aryl group which is unsubstituted or substituted in the para position with a suitable substituent; or a pharmaceutically acceptable prodrug or a pharmaceutically acceptable salt thereof.

9. A compound as claimed in claim 8 wherein the suitable substituent in the para position of the aryl group is a halogen atom, an alkoxy group or a heteroaryl group; or a pharmaceutically acceptable prodrug or a pharmaceutically acceptable salt thereof.

10. A compound as claimed in claim 2 wherein the carbon atom designated with "*" is in the R-configuration when X is $CH_2$, C=O, O, N—$R_3$, or $N^+(O^-)$-$R_4$ and in the S-configuration when X is S or S=O; or a pharmaceutically acceptable prodrug or a pharmaceutically acceptable salt thereof.

11. A compound as claimed in claim 9 wherein the suitable substituent in the para position of the aryl group is fluorine or chlorine; or a pharmaceutically acceptable prodrug or a pharmaceutically acceptable salt thereof.

12. A compound as claimed in claim 9 wherein the suitable substituent in the para position of the aryl group is a methoxy group; or a pharmaceutically acceptable prodrug or a pharmaceutically acceptable salt thereof.

13. A compound as claimed in claim 9 wherein the suitable substituent in the para position of the aryl group is an imidazolyl group; or a pharmaceutically acceptable prodrug or a pharmaceutically acceptable salt thereof.

14. A pharmaceutical composition comprising:
  (a) a therapeutically effective amount of a compound as defined in claim 1 or a pharmaceutically acceptable prodrug or a pharmaceutically acceptable salt thereof; and
  (b) a pharmaceutically acceptable carrier, diluent, vehicle or excipient.

15. A method of treating a mammalian disease condition mediated by metalloproteinase activity which comprises administering to a mammal in need thereof a therapeutically effective amount of a compound as defined in claim 1 or a pharmaceutically acceptable prodrug or a pharmaceutically acceptable salt thereof.

16. A method according to claim 15 wherein the mammalian disease condition is tumor growth, invasion or metastasis, or arthritis.

17. A method of inhibiting the activity of a metalloproteinase which comprises contacting the metalloproteinase with an effective amount of a compound as defined in claim 1 or a pharmaceutically acceptable prodrug or a pharmaceutically acceptable salt thereof.

18. A compound selected from the group consisting of 2(R)-N-hydro-1-(4-(4-chlorophenoxy) benzenesulfonyl)-4-(methanesulfonyl)piperazine-2-carboxamide; 2(R)-N-hydroxy-1-(4-(4-fluorophenoxy) benzenesulfonyl)-4-(methanesulfonyl)-piperazine-2-carboxamide; and 3(S)-N- hydroxy-4-(4-((pyrid-4-yl) oxy)benzenesulfonyl)-2,2-dimethyl-tetrahydro-2H-1,4-thiazine-3-carboxamide; and pharmaceutically acceptable salts and pharmaceutically acceptable prodrugs thereof.

19. A compound according to claim 18 which is 2(R)-N-hydroxy-1-(4-(4-fluorophenoxy)benzenesulfonyl)-4-(methanesulfonyl)piperazine-2-carboxamide; or a pharmaceutically acceptable salt or a pharmaceutically acceptable prodrug thereof.

20. A compound according to claim 18 which is 2(R)-N-hydroxy-1-(4-(4-chlorophenoxy)benzenesulfonyl)-4-(methanesulfonyl)piperazine-2-carboxamide; or a pharmaceutically acceptable salt or a pharmaceutically acceptable prodrug thereof.

21. A compound according to claim 18 which is 3(R)-N-hydroxy-4-(4-((pyrid-4-yl) oxy)benzenesulfonyl)-2,2-dimethyl-tetrahydro-2H-1,4-thaizine-3-carboxamide; or a pharmaceutically acceptable salt or a pharmaceutically acceptable prodrug thereof.

22. A compound according to claim 1 wherein no more than two said four ring atoms of Q are a heteroatom independently selected from O, N and S.

* * * * *

UNITED STATES PATENT AND TRADEMARK OFFICE
CERTIFICATE OF CORRECTION

PATENT NO. : 5,753,653
DATED : May 19, 1998
INVENTOR(S) : Bender et al.

It is certified that error appears in the above-identified patent and that said Letters Patent is hereby corrected as shown below:

Abstract, 4th line from the bottom "TNF-α" should read --TNFα convertase--.

Claim 4, col. 48, line 1, "alkylaminocarboyl" should read --alkylaminocarbonyl--.

Claim 4, col. 48, line 2, "dialkylaminocarbonyl" should read --dialkylaminocarbonyl group--.

Claim 18, col. 48, line 64, "hydro" should read --hydroxy--.

Claim 21, col. 50, line 3, "3(R)-N-" should read --3(S)-N- --.

Claim 21, col. 50, line 5, "thaizine" should read -- thiazine--.

Claim 22, col. 50, line 9, "two said" should read --two of said--.

Signed and Sealed this

Twelfth Day of January, 1999

Attest:

Attesting Officer

*Acting Commissioner of Patents and Trademarks*